(12) United States Patent
Heifetz

(10) Patent No.: US 9,168,290 B2
(45) Date of Patent: Oct. 27, 2015

(54) PRODUCT AND PROCESS FOR MUCUS VISCOSITY NORMALIZATION

(71) Applicant: OrPro Therapeutics, Inc., San Diego, CA (US)

(72) Inventor: Peter B. Heifetz, San Diego, CA (US)

(73) Assignee: OrPro Therapeutics, Inc., San Diego, CA (US)

( * ) Notice: Subject to any disclaimer, the term of this patent is extended or adjusted under 35 U.S.C. 154(b) by 2 days.

(21) Appl. No.: 14/216,568

(22) Filed: Mar. 17, 2014

(65) Prior Publication Data
US 2014/0271599 A1  Sep. 18, 2014

Related U.S. Application Data

(60) Provisional application No. 61/792,198, filed on Mar. 15, 2013.

(51) Int. Cl.
*A61K 38/44* (2006.01)

(52) U.S. Cl.
CPC ........... *A61K 38/44* (2013.01); *C12Y 108/0401* (2013.01)

(58) Field of Classification Search
None
See application file for complete search history.

(56) References Cited

U.S. PATENT DOCUMENTS

| | | | |
|---|---|---|---|
| 3,091,569 A | 5/1963 | Sheffner | |
| 3,502,779 A | 3/1970 | Dye et al. | |
| 3,683,069 A | 8/1972 | Hooreman | |
| 4,771,036 A | 9/1988 | Pigiet et al. | |
| 5,380,758 A | 1/1995 | Stamler et al. | |
| 5,908,611 A | 6/1999 | Gottlieb et al. | |
| 5,925,334 A | 7/1999 | Rubin et al. | |
| 5,985,261 A | 11/1999 | White et al. | |
| 6,303,642 B1 | 10/2001 | Susilo et al. | |
| 7,195,766 B2 * | 3/2007 | White | 424/185.1 |
| 7,534,438 B2 * | 5/2009 | White | 424/185.1 |
| 2005/0260140 A1 | 11/2005 | White et al. | |
| 2006/0148057 A1 * | 7/2006 | Min et al. | 435/191 |
| 2009/0311231 A1 | 12/2009 | White | |

FOREIGN PATENT DOCUMENTS

| WO | WO 91/04320 | 4/1991 |
|---|---|---|
| WO | WO 02/078683 | 10/2002 |

OTHER PUBLICATIONS

Brown et al., Eur. Respir. J., 1996, 9, pp. 334-339.*
Brown et al., Eur. Respir. J., 1996, 9, 334-339.*
Arner, E. et al., "Physiological functions of thioredoxin and thioredoxin reductase," Eur. J. Biochem., Oct. 2000, vol. 267(20), pp. 6102-6109.
Bell et al., "Role of the cystine-knot motif at the C-terminus of rat mucin protein Muc2 in dimer formation and secretion," Biochem J., Jul. 2001, vol. 357, pp. 203-209.
Brown et al. "Pulmonary dysfunction in cystic fibrosis is associated with oxidative stress," European Respiratory Journal, Feb. 1, 1996, vol. 9, No. 2, pp. 334-339.
Del Val, D. et al., Thioredoxin-(dithiol-)linked inactivation of elastase, Mol. Immunol., Jan. 2001, vol. 38, pp. 759-763.
Fuchs et al., "Effect of aerosolized recombinant human DNase on exacerbations of respiratory symptoms and on pulmonary function in patients with cystic fibrosis. The Pulmozyme Study Group," N. Engl J. Med., Sep. 1994, vol. 331(10), pp. 637-642.
Fuloria et al., "Evaluating the efficacy of mucoactive aerosol therapy," Respir Care, Jul. 2000, vol. 45(7), pp. 868-873.
Hara et al. "Cell-Surface Thioredoxin-1: Possible Involvement in Thiol-Mediated Leukocyte-Endothelial Cell Interaction Through Lipid Rafts," Antioxidants & Redox Signaling, 2007, vol. 9, No. 9, pp. 1427-1437.
Harper et al., "Activation of nuclear factor-kappa b transcriptional activity in airway epithelial cells by thioredoxin but not by N-acetyl-cysteine and glutathione," Am. J. Respir. Cell Mol. Biol., Aug. 2001, vol. 25, pp. 178-185.
Holmgren "Thioredoxin," Annual Reviews of Biochemistry, 1985, vol. 54, pp. 237-271.
Isowa et al. "Human Thioredoxin Attenuates Hypoxia-Reoxygenation Injury of Murine Endothelial Cells in a Thiol-Free Condition." Journal of Cellular Physiology, 2000, vol. 182, pp. 33-40.
Kondo et al. "Lipid Raft-Mediated Uptake of Cysteine-Modified Thioredoxin-1: Apoptosis Enhancement by Inhibiting the Endogenous Thioredoxin-1," Antioxidants & Redox Signaling, 2007, vol. 9, No. 9, pp. 1439-1448.
Lamoureux et al., "Synthesis of Dithiols as Reducing Agents for Disulfides in Neutral Aqueous Solutions and Comparison of Reduction Potentials," J. Org. Chem., 1993, vol. 58, pp. 633-641.
Matsuo et al. "Extracellular thioredoxin: A therapeutic tool to combat inflammation," Cytokine & Growth Factor Reviews, Aug. 2013, vol. 24, No. 4, pp. 345-353.
Matthias et al. "Disulfide exchange in domain 2 of CD4 is required for entry of HIV-1," Nature Immunology, Aug. 2002, vol. 3, No. 8, pp. 727-732.
Nakamura et al. "Thioredoxin 1 delivery as new therapeutics," Advanced Drug Delivery Reviews, 2009, vol. 61, pp. 303-309.
Oblong et al., "Purification of human thioredoxin reductase: properties and characterization by absorption and circular dichroism spectroscopy," Biochemistry, Jul. 1993, vol. 32, pp. 7271-7277.
Rancourt, R. et al., "Thioredoxin liquefies and decreases the viscoelasticity of cystic fibrosis sputum," American Journal of Physiology, May 2004, vol. 286(5), pp. L931-L938.
Schwertassek et al. "Selective redox regulation of cytokine receptor signaling by extracellular thioredoxin-1," The EMBO Journal, 2007, vol. 26, No. 13, pp. 3086-3097.
Serrato et al. "AtCXXS: atypical members of the Arabidopsis thaliana thioredoxin h family with a remarkably high disulfide isomerase activity," Physiologia Plantarum, 2008, vol. 133, pp. 611-622.
Sun et al., "Additive effect of dornase alfa and Nacystelyn on transportability and viscoelasticity of cystic fibrosis sputum," Can Respir J., Nov.-Dec. 2002, vol. 9(6), pp. 401-406.

(Continued)

Primary Examiner — Karlheinz R Skowronek
Assistant Examiner — Roy Teller
(74) Attorney, Agent, or Firm — Sheridan Ross P.C.

(57) ABSTRACT

Disclosed are compositions and methods for decreasing the viscosity and/or cohesiveness of and/or increasing the liquefaction of excessively or abnormally viscous or cohesive mucus or sputum. The composition contains a protein or peptide containing a thioredoxin monocysteinic active site in a reduced state and optionally further contains a reducing system.

17 Claims, 3 Drawing Sheets

(56) References Cited

OTHER PUBLICATIONS

Tabachnik et al., "Biochemical and rheological characterization of sputum mucins from a patient with cystic fibrosis," J. Biol. Chem., Jul. 1981, vol. 256(14), pp. 7161-65.

Tang et al., "Thiol oxidation of actin produces dimers that enhance the elasticity of the F-actin network," Biophys. J., Apr. 1999, vol. 76, pp. 2208-2215.

Wang et al., "Oxidative stress disrupts glucocorticoid hormone-dependent transcription of the amiloride-sensitive epithelial sodium channel alpha-subunit in lung epithelial cells through ERK-dependent and thioredoxin-sensitive pathways," J. Biol. Chem., Mar. 2000, vol. 275(12), pp. 8600-8609.

Xu et al. "Role of thioredoxin in lung disease,:" Pulmonary Pharmacology & Therapeutics, 2012, vol. 25, pp. 154-162.

Yashiro et al. "Redox-Active Protein Thioredoxin-1 Administration Ameliorates Influenza A Virus (H1N1)-Induced Acute Lung Injury in Mice," Critical Care Medicine, Jan. 2013, vol. 41, No. 1, pp. 171-181.

Zhang et al. "Protective effect of thioredoxin perfusion but not inhalation in warm ischemic-reperfused rat lungs," Redox Report, 2009, vol. 14, No. 2, pp. 75-81.

International Search Report and Written Opinion for International (PCT) Patent Application No. PCT/US14/30545, mailed Nov. 5, 2014 16 pages.

International Search Report and Written Opinion for International (PCT) Patent Application No. PCT/US14/30545, mailed Apr. 2, 2015 16 pages.

\* cited by examiner

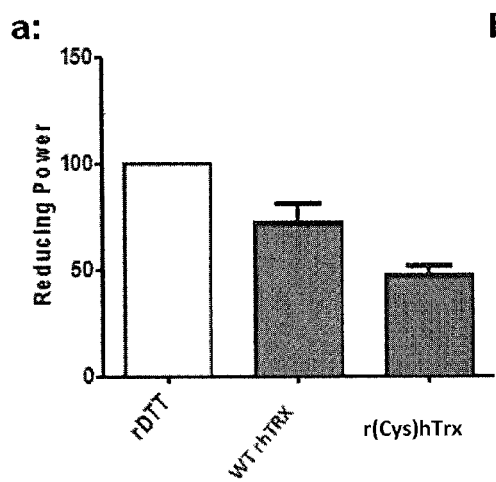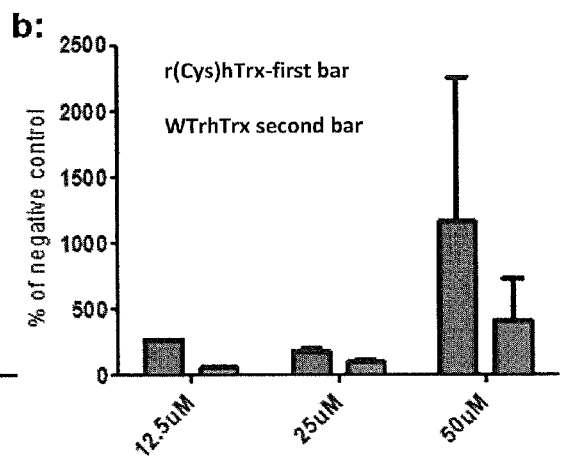
Fig. 1a                    Fig. 1b

SEQUENCE LISTING

<160> NUMBER OF SEQ ID NOS: 27

<210> SEQ ID NO 1
<211> LENGTH: 4
<212> TYPE: PRT
<213> ORGANISM: Artificial sequence
<220> FEATURE:
<223> OTHER INFORMATION: synthetic peptide motif

<400> SEQUENCE: 1

Cys Gly Pro Cys
1

<210> SEQ ID NO 2
<211> LENGTH: 6
<212> TYPE: PRT
<213> ORGANISM: Artificial sequence
<220> FEATURE:
<223> OTHER INFORMATION: synthetic peptide motif
<220> FEATURE:
<221> NAME/KEY: misc_feature
<222> LOCATION: (1)..(6)
<223> OTHER INFORMATION: Xaa = any amino acid

<400> SEQUENCE: 2

Xaa Cys Gly Pro Cys Xaa
1               5

<210> SEQ ID NO 3
<211> LENGTH: 6
<212> TYPE: PRT
<213> ORGANISM: Artificial sequence
<220> FEATURE:
<223> OTHER INFORMATION: synthetic peptide motif

<400> SEQUENCE: 3

Trp Cys Gly Pro Cys Lys
1               5

<210> SEQ ID NO 4
<211> LENGTH: 109
<212> TYPE: PRT
<213> ORGANISM: Pseudomonas syringae

<400> SEQUENCE: 4

Met Ser Asn Asp Leu Ile Lys His Val Thr Asp Ala Ser Phe Glu Ala
1               5                   10                  15

Asp Val Leu Lys Ala Asp Gly Ala Val Leu Val Asp Tyr Trp Ala Glu
            20                  25                  30

Trp Cys Gly Pro Cys Lys Met Ile Ala Pro Val Leu Asp Glu Ile Ala
        35                  40                  45

Thr Thr Tyr Ala Gly Lys Leu Thr Ile Ala Lys Leu Asn Ile Asp Glu
    50                  55                  60

Asn Gln Glu Thr Pro Ala Lys His Gly Val Arg Gly Ile Pro Thr Leu
65                  70                  75                  80

Met Leu Phe Lys Asn Gly Asn Val Glu Ala Thr Lys Val Gly Ala Leu
                85                  90                  95

Ser Lys Ser Gln Leu Ala Ala Phe Leu Asp Ala Asn Ile
            100                 105

<210> SEQ ID NO 5
<211> LENGTH: 104
<212> TYPE: PRT
<213> ORGANISM: Porphyromonas gingivalis

<400> SEQUENCE: 5

Met Ala Leu Gln Ile Thr Asp Ala Thr Phe Asp Gly Leu Val Ala Glu
1               5                   10                  15

Gly Lys Pro Met Val Val Asp Phe Trp Ala Thr Trp Cys Gly Pro Cys
            20                  25                  30

Arg Met Val Gly Pro Ile Ile Asp Glu Leu Ala Ala Glu Tyr Glu Gly
        35                  40                  45

Arg Ala Ile Ile Gly Lys Val Asp Val Asp Ala Asn Thr Glu Leu Pro
    50                  55                  60

Met Lys Tyr Gly Val Arg Asn Ile Pro Thr Ile Leu Phe Ile Lys Asn
65                  70                  75                  80

Gly Glu Val Val Lys Lys Leu Val Gly Ala Gln Ser Lys Asp Val Phe
                85                  90                  95

Lys Lys Glu Leu Asp Ala Leu Phe
            100

<210> SEQ ID NO 6
<211> LENGTH: 103
<212> TYPE: PRT
<213> ORGANISM: Listeria monocytogenes

<400> SEQUENCE: 6

Met Val Lys Glu Ile Thr Asp Ala Thr Phe Glu Gln Glu Thr Ser Glu
1               5                   10                  15

Gly Leu Val Leu Thr Asp Phe Trp Ala Thr Trp Cys Gly Pro Cys Arg
            20                  25                  30

Met Val Ala Pro Val Leu Glu Glu Ile Gln Glu Glu Arg Gly Glu Ala
        35                  40                  45

Leu Lys Ile Val Lys Met Asp Val Asp Glu Asn Pro Glu Thr Pro Gly
    50                  55                  60

Ser Phe Gly Val Met Ser Ile Pro Thr Leu Leu Ile Lys Lys Asp Gly
65                  70                  75                  80

Glu Val Val Glu Thr Ile Ile Gly Tyr Arg Pro Lys Glu Glu Leu Asp
                85                  90                  95

Glu Val Ile Asn Lys Tyr Val
            100

<210> SEQ ID NO 7
<211> LENGTH: 103
<212> TYPE: PRT
<213> ORGANISM: Saccharomyces cerevisiae

<400> SEQUENCE: 7

Met Val Thr Gln Phe Lys Thr Ala Ser Glu Phe Asp Ser Ala Ile Ala
1               5                   10                  15

Gln Asp Lys Leu Val Val Val Asp Phe Tyr Ala Thr Trp Cys Gly Pro
            20                  25                  30

Cys Lys Met Ile Ala Pro Met Ile Glu Lys Phe Ser Glu Gln Tyr Pro
        35                  40                  45

Gln Ala Asp Phe Tyr Lys Leu Asp Val Asp Glu Leu Gly Asp Val Ala
    50                  55                  60

Gln Lys Asn Glu Val Ser Ala Met Pro Thr Leu Leu Leu Phe Lys Asn
65                  70                  75                  80

Gly Lys Glu Val Ala Lys Val Val Gly Ala Asn Pro Ala Ala Ile Lys
                85                  90                  95

```
Gln Ala Ile Ala Ala Asn Ala
            100

<210> SEQ ID NO 8
<211> LENGTH: 105
<212> TYPE: PRT
<213> ORGANISM: Gallus gallus

<400> SEQUENCE: 8

Met Val Lys Ser Val Gly Asn Leu Ala Asp Phe Glu Ala Glu Leu Lys
1               5                   10                  15

Ala Ala Gly Glu Lys Leu Val Val Asp Phe Ser Ala Thr Trp Cys
            20                  25                  30

Gly Pro Cys Lys Met Ile Lys Pro Phe Phe His Ser Leu Cys Asp Lys
        35                  40                  45

Phe Gly Asp Val Val Phe Ile Glu Ile Asp Val Asp Asp Ala Gln Asp
    50                  55                  60

Val Ala Thr His Cys Asp Val Lys Cys Met Pro Thr Phe Gln Phe Tyr
65                  70                  75                  80

Lys Asn Gly Lys Lys Val Gln Glu Phe Ser Gly Ala Asn Lys Glu Lys
                85                  90                  95

Leu Glu Glu Thr Ile Lys Ser Leu Val
            100                 105

<210> SEQ ID NO 9
<211> LENGTH: 105
<212> TYPE: PRT
<213> ORGANISM: Mus musculus

<400> SEQUENCE: 9

Met Val Lys Leu Ile Glu Ser Lys Glu Ala Phe Gln Glu Ala Leu Ala
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Cys Asp Lys
        35                  40                  45

Tyr Ser Asn Val Val Phe Leu Glu Val Asp Val Asp Asp Cys Gln Asp
    50                  55                  60

Val Ala Ala Asp Cys Glu Val Lys Cys Met Pro Thr Phe Gln Phe Tyr
65                  70                  75                  80

Lys Lys Gly Gln Lys Val Gly Glu Phe Ser Gly Ala Asn Lys Glu Lys
                85                  90                  95

Leu Glu Ala Ser Ile Thr Glu Tyr Ala
            100                 105

<210> SEQ ID NO 10
<211> LENGTH: 105
<212> TYPE: PRT
<213> ORGANISM: Rattus norvegicus

<400> SEQUENCE: 10

Met Val Lys Leu Ile Glu Ser Lys Glu Ala Phe Gln Glu Ala Leu Ala
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Cys Asp Lys
        35                  40                  45

Tyr Ser Asn Val Val Phe Leu Glu Val Asp Val Asp Asp Cys Gln Asp
```

```
                    50                  55                  60
Val Ala Asp Cys Glu Val Lys Cys Met Pro Thr Phe Gln Phe Tyr
 65                  70                  75                  80

Lys Lys Gly Gln Lys Val Gly Glu Phe Ser Gly Ala Asn Lys Glu Lys
                 85                  90                  95

Leu Glu Ala Thr Ile Thr Glu Phe Ala
                100                 105

<210> SEQ ID NO 11
<211> LENGTH: 105
<212> TYPE: PRT
<213> ORGANISM: Bos taurus

<400> SEQUENCE: 11

Met Val Lys Gln Ile Glu Ser Lys Tyr Ala Phe Gln Glu Ala Leu Asn
 1               5                  10                  15

Ser Ala Gly Glu Lys Leu Val Val Asp Phe Ser Ala Thr Trp Cys
                 20                  25                  30

Gly Pro Cys Lys Met Ile Lys Pro Phe Phe His Ser Leu Ser Glu Lys
                 35                  40                  45

Tyr Ser Asn Val Val Phe Leu Glu Val Asp Val Asp Asp Cys Gln Asp
                 50                  55                  60

Val Ala Ala Glu Cys Glu Val Lys Cys Met Pro Thr Phe Gln Phe Phe
 65                  70                  75                  80

Lys Lys Gly Gln Lys Val Gly Glu Phe Ser Gly Ala Asn Lys Glu Lys
                 85                  90                  95

Leu Glu Ala Thr Ile Asn Glu Leu Ile
                100                 105

<210> SEQ ID NO 12
<211> LENGTH: 105
<212> TYPE: PRT
<213> ORGANISM: Homo sapiens

<400> SEQUENCE: 12

Met Val Lys Gln Ile Glu Ser Lys Thr Ala Phe Gln Glu Ala Leu Asp
 1               5                  10                  15

Ala Ala Gly Asp Lys Leu Val Val Asp Phe Ser Ala Thr Trp Cys
                 20                  25                  30

Gly Pro Cys Lys Met Ile Lys Pro Phe Phe His Ser Leu Ser Glu Lys
                 35                  40                  45

Tyr Ser Asn Val Ile Phe Leu Glu Val Asp Val Asp Asp Cys Gln Asp
                 50                  55                  60

Val Ala Ser Glu Cys Glu Val Lys Cys Met Pro Thr Phe Gln Phe Phe
 65                  70                  75                  80

Lys Lys Gly Gln Lys Val Gly Glu Phe Ser Gly Ala Asn Lys Glu Lys
                 85                  90                  95

Leu Glu Ala Thr Ile Asn Glu Leu Val
                100                 105

<210> SEQ ID NO 13
<211> LENGTH: 134
<212> TYPE: PRT
<213> ORGANISM: Arabidopsis thaliana

<400> SEQUENCE: 13

Met Gly Gly Ala Leu Ser Thr Val Phe Gly Ser Gly Glu Asp Ala Ala
 1               5                  10                  15
```

```
Ala Ala Gly Thr Glu Ser Ser Glu Pro Ser Arg Val Leu Lys Phe Ser
            20                  25                  30

Ser Ser Ala Arg Trp Gln Leu His Phe Asn Glu Ile Lys Glu Ser Asn
        35                  40                  45

Lys Leu Leu Val Val Asp Phe Ser Ala Ser Trp Cys Gly Pro Cys Arg
    50                  55                  60

Met Ile Glu Pro Ala Ile His Ala Met Ala Asp Lys Phe Asn Asp Val
65                  70                  75                  80

Asp Phe Val Lys Leu Asp Val Asp Glu Leu Pro Asp Val Ala Lys Glu
                85                  90                  95

Phe Asn Val Thr Ala Met Pro Thr Phe Val Leu Val Lys Arg Gly Lys
            100                 105                 110

Glu Ile Glu Arg Ile Ile Gly Ala Lys Lys Asp Glu Leu Glu Lys Lys
        115                 120                 125

Val Ser Lys Leu Arg Ala
    130

<210> SEQ ID NO 14
<211> LENGTH: 167
<212> TYPE: PRT
<213> ORGANISM: Zea mays

<400> SEQUENCE: 14

Met Ala Met Glu Thr Cys Phe Arg Ala Trp Ala Leu His Ala Pro Ala
1               5                   10                  15

Gly Ser Lys Asp Arg Leu Leu Val Gly Asn Leu Val Leu Pro Ser Lys
            20                  25                  30

Arg Ala Leu Ala Pro Leu Ser Val Gly Arg Val Ala Thr Arg Arg Pro
        35                  40                  45

Arg His Val Cys Gln Ser Lys Asn Ala Val Asp Glu Val Val Val Ala
    50                  55                  60

Asp Glu Lys Asn Trp Asp Gly Leu Val Met Ala Cys Glu Thr Pro Val
65                  70                  75                  80

Leu Val Glu Phe Trp Ala Pro Trp Cys Gly Pro Cys Arg Met Ile Ala
                85                  90                  95

Pro Val Ile Asp Glu Leu Ala Lys Asp Tyr Ala Gly Lys Ile Thr Cys
            100                 105                 110

Cys Lys Val Asn Thr Asp Asp Ser Pro Asn Val Ala Ser Thr Tyr Gly
        115                 120                 125

Ile Arg Ser Ile Pro Thr Val Leu Ile Phe Lys Gly Gly Glu Lys Lys
    130                 135                 140

Glu Ser Val Ile Gly Ala Val Pro Lys Ser Thr Leu Thr Thr Leu Ile
145                 150                 155                 160

Asp Lys Tyr Ile Gly Ser Ser
                165

<210> SEQ ID NO 15
<211> LENGTH: 172
<212> TYPE: PRT
<213> ORGANISM: Oryza sativa

<400> SEQUENCE: 15

Met Ala Leu Glu Thr Cys Phe Arg Ala Trp Ala Thr Leu His Ala Pro
1               5                   10                  15

Gln Pro Pro Ser Ser Gly Gly Ser Arg Asp Arg Leu Leu Leu Ser Gly
            20                  25                  30
```

```
Ala Gly Ser Ser Gln Ser Lys Pro Arg Leu Ser Val Ala Ser Pro Ser
            35                  40                  45
Pro Leu Arg Pro Ala Ser Arg Phe Ala Cys Gln Cys Ser Asn Val Val
        50                  55                  60
Asp Glu Val Val Val Ala Asp Glu Lys Asn Trp Asp Ser Met Val Leu
65                  70                  75                  80
Gly Ser Glu Ala Pro Val Leu Val Glu Phe Trp Ala Pro Trp Cys Gly
                85                  90                  95
Pro Cys Arg Met Ile Ala Pro Val Ile Asp Glu Leu Ala Lys Glu Tyr
            100                 105                 110
Val Gly Lys Ile Lys Cys Cys Lys Val Asn Thr Asp Asp Ser Pro Asn
        115                 120                 125
Ile Ala Thr Asn Tyr Gly Ile Arg Ser Ile Pro Thr Val Leu Met Phe
130                 135                 140
Lys Asn Gly Glu Lys Lys Glu Ser Val Ile Gly Ala Val Pro Lys Thr
145                 150                 155                 160
Thr Leu Ala Thr Ile Ile Asp Lys Tyr Val Ser Ser
                165                 170

<210> SEQ ID NO 16
<211> LENGTH: 4
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (2)..(3)
<223> OTHER INFORMATION: Xaa = any amino acid other than cysteine

<400> SEQUENCE: 16

Cys Xaa Xaa Cys
1

<210> SEQ ID NO 17
<211> LENGTH: 4
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (2)..(4)
<223> OTHER INFORMATION: Xaa = any amino acid other than cysteine

<400> SEQUENCE: 17

Cys Xaa Xaa Xaa
1

<210> SEQ ID NO 18
<211> LENGTH: 4
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (4)..(4)
<223> OTHER INFORMATION: Xaa = any amino acid other than cysteine

<400> SEQUENCE: 18

Cys Gly Pro Xaa
1
```

```
<210> SEQ ID NO 19
<211> LENGTH: 6
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (1)..(1)
<223> OTHER INFORMATION: Xaa = any amino acid other than cysteine
<220> FEATURE:
<221> NAME/KEY: MISC_FEATURE
<222> LOCATION: (3)..(6)
<223> OTHER INFORMATION: Xaa = any amino acid other than cysteine

<400> SEQUENCE: 19

Xaa Cys Xaa Xaa Xaa Xaa
1               5

<210> SEQ ID NO 20
<211> LENGTH: 6
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (1)..(1)
<223> OTHER INFORMATION: Xaa = any amino acid other than cysteine
<220> FEATURE:
<221> NAME/KEY: MISC_FEATURE
<222> LOCATION: (3)..(4)
<223> OTHER INFORMATION: Xaa = any amino acid other than cysteine
<220> FEATURE:
<221> NAME/KEY: MISC_FEATURE
<222> LOCATION: (6)..(6)
<223> OTHER INFORMATION: Xaa = any amino acid other than cysteine

<400> SEQUENCE: 20

Xaa Cys Xaa Xaa Cys Xaa
1               5

<210> SEQ ID NO 21
<211> LENGTH: 6
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (1)..(1)
<223> OTHER INFORMATION: Xaa = any amino acid other than cysteine
<220> FEATURE:
<221> NAME/KEY: MISC_FEATURE
<222> LOCATION: (5)..(6)
<223> OTHER INFORMATION: Xaa = any amino acid other than cysteine

<400> SEQUENCE: 21

Xaa Cys Gly Pro Xaa Xaa
1               5

<210> SEQ ID NO 22
<211> LENGTH: 6
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (1)..(1)
<223> OTHER INFORMATION: Xaa = any amino acid other than cysteine
<220> FEATURE:
```

```
<221> NAME/KEY: MISC_FEATURE
<222> LOCATION: (6)..(6)
<223> OTHER INFORMATION: Xaa = any amino acid other than cysteine

<400> SEQUENCE: 22

Xaa Cys Gly Pro Cys Xaa
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (5)..(5)
<223> OTHER INFORMATION: Xaa = any amino acid other than cysteine

<400> SEQUENCE: 23

Trp Cys Gly Pro Xaa Lys
1               5

<210> SEQ ID NO 24
<211> LENGTH: 4
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (2)..(3)
<223> OTHER INFORMATION: Xaa = any amino acid other than cysteine

<400> SEQUENCE: 24

Cys Xaa Xaa Ser
1

<210> SEQ ID NO 25
<211> LENGTH: 6
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (1)..(1)
<223> OTHER INFORMATION: Xaa = any amino acid other than cysteine
<220> FEATURE:
<221> NAME/KEY: MISC_FEATURE
<222> LOCATION: (3)..(4)
<223> OTHER INFORMATION: Xaa = any amino acid other than cysteine
<220> FEATURE:
<221> NAME/KEY: MISC_FEATURE
<222> LOCATION: (6)..(6)
<223> OTHER INFORMATION: Xaa = any amino acid other than cysteine

<400> SEQUENCE: 25

Xaa Cys Xaa Xaa Ser Xaa
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic peptide motif
<220> FEATURE:
<221> NAME/KEY: MISC_FEATURE
<222> LOCATION: (1)..(1)
<223> OTHER INFORMATION: Xaa = any amino acid other than cysteine
```

```
<220> FEATURE:
<221> NAME/KEY: MISC_FEATURE
<222> LOCATION: (6)..(6)
<223> OTHER INFORMATION: Xaa = any amino acid other than cysteine

<400> SEQUENCE: 26

Xaa Cys Gly Pro Ser Xaa
1               5

<210> SEQ ID NO 27
<211> LENGTH: 6
<212> TYPE: PRT
<213> ORGANISM: Artificial Sequence
<220> FEATURE:
<223> OTHER INFORMATION: synthetic peptide motif

<400> SEQUENCE: 27

Trp Cys Gly Pro Ser Lys
1               5
```

PRODUCT AND PROCESS FOR MUCUS VISCOSITY NORMALIZATION

CROSS-REFERENCE TO RELATED APPLICATIONS

This application claims the benefit of priority under 35 U.S.C. 119(e) to U.S. Provisional Application Ser. No. 61/792,198, filed Mar. 15, 2013. The entire disclosure of U.S. Provisional Application Ser. No. 61/792,198, filed Mar. 15, 2013, is incorporated herein by reference.

REFERENCE TO SEQUENCE LISTING

This application contains a Sequence Listing submitted electronically as a text file by EFS-Web. The text file, named "7579-1_sequence_listing_ST25", has a size in bytes of 18 KB, and was recorded on 17 Mar. 2014. The information contained in the text file is incorporated herein by reference in its entirety pursuant to 37 CFR §1.52(e)(5).

FIELD OF THE INVENTION

This invention relates generally to the use of a protein or peptide containing a thioredoxin monocysteinic active site in a reduced state to reduce viscosity and to induce, enhance and/or increase the liquefaction of mucus or sputum.

BACKGROUND OF THE INVENTION

A large unmet medical need exists for safe, well-tolerated and effective drugs for the treatment of patients with cystic fibrosis (CF), COPD/emphysema, bronchiectasis, severe asthma and other serious obstructive pulmonary diseases. These diseases are characterized by overproduction of thickened mucus resulting in impaired lung function (reviewed in Evans, C. M. and Koo, J. S., *Pharmacology & Therapeutics* 121: 332-348, 2009). Poor clearance of abnormal, sticky mucus is associated with chronic infection and premature death, especially in CF. Despite advances in antibiotic therapy and other treatments, improved mucus clearance remains a central clinical treatment objective even while our understanding of the mechanisms underlying mucus transportability are still limited (Verdugo, P., *Cold Spring Harb Perspect Med* 2012; 2:a009597).

Mucus is a continuously-secreted supramolecular polymer gel that forms a protective barrier on epithelial surfaces and is responsible via ciliary action and cough for transporting inhaled debris and bacteria out of the lung (Knowles, M. R. and Boucher, R. C., *J Clin Invest* 109:571-577, 2002; Cone, R. A., *Adv Drug Deliv Rev* 61:75-85, 2009). Proper viscoelasticity and hydration of the mucus layer, which enables efficient mucociliary transport, is therefore critical to mucus function and the prevention of infection and inflammation. Normal mucus consists of mostly water (97%) with the remaining solids comprising mucin proteins, non-mucin proteins, salts, lipids and cellular debris (Fahy, J. V. and Dickey, B. F., *N Engl J Med* 363:2233-47, 2010). The polymeric mucin glycoproteins MUC5AC and MUC5B are primarily responsible for the viscoelastic properties of the respiratory mucus gel (Matsui et al., *Cell* 95:1005-1015, 1998; reviewed in Kreda, et al., *Cold Spring Harb Perspect Med* 2012; 2:a009589). The O-linked glycan hydroxyl groups attached to mucins contribute water-binding, while the mucins themselves form an entangled network (Verdugo et al., *Biorheology* 20:223-230, 1983) that may also involve covalent and non-covalent interchain cross-linking as suggested from detailed studies of the digestive tract mucin MUC2 (Ambort et al., *Biochem J* 436:61-70, 2011). Mucins are unusually rich in Cys amino acids, with human MUC5AC containing a remarkable 295 Cys residues out of a total of 5030 amino acids (www.uniprot.org/uniprot/P98088). Mucin Cys residues located near the N and C termini are thought to be involved in formation of interchain disulfide linkages between mucin subunits, while the role of the internal Cys residues is less clear (Thornton et al., *Annu Rev Physiol* 70:459-486, 2008). Some are located in a 'Cys Knot' region and might readily form intramolecular disulfide bonds that could play a role in facilitating the non-covalent entanglement central to the mucus gel mesh structure (Fahy, J. V. and Dickey, B. F., *N Engl J Med* 363:2233-47, 2010).

Recent work (Button et al., *Science* 337:937-941, 2012) has led to a new model of the structure of the mucosal surface based on the finding that certain mucins, once thought to be membrane bound on epithelial cells, are actually tethered to membranes on cilia themselves. The implication of this model is that the mobile mucus layer overlays an even denser periciliary layer, described as a "gel-on-brush". The model explains elegantly how liquid moves between the two layers with the mucus acting as a reservoir, and establishes a new paradigm for understanding the role of mucus osmotic modulus in determining the functionality of mucociliary transport and mucus layer hydration. The model also provides a framework to understand how excess disulfide bonding in the mucus protein scaffold might cause increased mucus layer osmotic modulus, which in turn dehydrates the underlying ciliary layer and severely constrains normal mucus transport. Such a scenario may underpin a substantial portion of the disease mechanism of CF.

CF is an autosomal recessive condition. The symptoms of CF result from defects in CFTR, the Cystic Fibrosis Transmembrane Conductance Regulator, a key epithelial membrane transporter for monovalent negatively charged ions, primarily chloride (Riordan, et al., *Science* 245: 1066-1073), but also bicarbonate and glutathione. Mutations leading to CF, of which over 1700 are known (www.genet.sickkids.on.ca/cftr/), include those causing complete loss of CFTR (the case for the most common CF genotype) as well as point mutations resulting in partial or full loss of anion transport activity. In addition, as a result of the defects in CFTR, epithelia within the body are impermeable to chloride ion transport (Boucher et al., *Lung* 161:1-17, 1983; Welsh, *Physiol Rev* 67:11443-1184, 1987). Although several organs are affected, including pancreas, intestine, and male genital tract, complications within the lung account for 95% of the morbidity and mortality (Means, M. Cystic Fibrosis: the first 50 years. In: *Cystic Fibrosis-Current Topics* Volume 1, edited by Dodge J A, Brock D J H, and Widdicombe J H. Chichester: Wiley and Sons, 1992, p. 217-250). In lung impaired by the disease, chloride transport into the airway lumen leads to excessive absorption of $Na^+$ and fluid, reducing the volume of airway surface liquid (Jiang et al., *Science* 262:424-427, 1993). Attempts have failed, however, to restore chloride channel activity to compensate for the effects caused by the non-functioning CFTR, e.g. via agonists of the $P2Y_2$ subtype of purinergic receptor (Ratjen, F. et al., *J Cyst Fibros* 11:539-49, 2012). This suggests that non-chloride effects of CFTR might be more significant than originally thought.

In oxidizing environments like the lung, disulfide bonds are readily formed between adjacent oxidized Cys residues such as those present in great abundance on mucin proteins. These bonds are highly stable, and disrupting (i.e. reducing) them in order to restore the Cys residues to their free thiol form requires the action of potent chemical or biological reductants. In the healthy lung, excess disulfide bond formation is countered primarily by the reduced form of the biological reductant glutathione (GSH), a Cys-containing tripeptide that is secreted in large amounts into the mucus layer (Cantin et al., *J Appl Physiol* 63:152-157, 1987), and may play a key role in maintaining a normal disulfide bond vs. free Cys thiol equilibrium in mucins. Secretion of GSH onto the airway surface is highly dependent upon CFTR, which both directly and indirectly facilitates GSH export (reviewed in Ballatori et al., *Biol Chem* 390: 191-214, 2009). Consequently, levels of pulmonary GSH in CF patients may be 30% or less than levels found in normal individuals (Roum et al., *J Appl Physiol* 75:2419-24, 2003; Wetmore D. R. et al., *J Biol Chem* 285:30516-22, 2010). CFTR is also responsible for secretion of bicarbonate anions, and the resulting deficiency of bicarbonate in the CF lung appears to contribute to disease. A primary chemical effect of bicarbonate is to raise pH. Since reduction of disulfide bonds by thiol-containing reductants requires the formation of an attacking deprotonated thiolate, which is inhibited at low pH where the protonated thiol form is favored (Singh and Whitesides, In: *Sulphur-containing Functional Groups,* 5: pp. 633-58, John Wiley & Sons, 1993), synergy between the activities of bicarbonate and GSH (as well as other biological reductants known to be present in the airway surface environs) is likely. Measured pH in CF tracheobronchial secretions is up to 0.6 units lower vs non-diseased (Song et al., *Am J Physiol Cell Physiol* 290:C741-C749), consistent with an environment in the CF lung where reductant is both present in limiting supply as well as being less active due to an impaired ability to form disulfide-attacking thiolates. Taken together with the enormous number of clustered Cys present in mucins, mucus in the oxidizing respiratory environment is thus poised to be in a more highly disulfide-bonded state if either secreted reductant levels become limiting, or if mucin proteins are produced and secreted in excess resulting in a superabundance of disulfide-bondable Cys. Both situations are known to occur in CF and certain other obstructive pulmonary diseases: mucus proteins are over-produced in response to lung stress (Rogers, *Resp Care* 52:1134-1149), and 70% or more of GSH secretion can be blocked as a consequence of defects in CFTR (Roum et al., *J Appl Physiol* 75:2419-24, 2003; Wetmore D. R. et al., *J Biol Chem* 285:30516-22, 2010).

This potential for excess mucus disulfide-bonding as well as general redox imbalance to play a mechanistic role in CF has led to the clinical evaluation of various thiol-containing agents as mucolytic drugs. These include N-acetylcysteine (NAC) and Nacystelyn (NAL; N-acetylcysteine+L-lysine) (Hurst et al., *Am Rev Respir Dis,* 96:962-970, 1967; Dasgupta and King, *Pediatr Pulmonol,* 22:161-166, 1996; Nash, E. F., et al., *Cochrane Database of Systematic Reviews,* 2010(12): 1-49, 2009) as well as reduced glutathione itself (Bishop, C., et al., *CHEST Journal,* 127(1): 308-317, 2005; Griese, M., et al., *Am J Resp Crit Care Med* 169(7):822-828, 2004; Griese, M., et al., *Am J Resp Crit Care Med* 188(1):83-89, 2013; Roum, J. H., et al., *J Appl Physiol,* 87:438-443, 1999). While largely safe, to date these small-molecule agents have not exhibited clear clinical benefits in either oral or inhaled forms (reviewed in Nash, E. F., et al., *Cochrane Database of Systematic Reviews,* 2010(12): 1-49, 2009). Much of this lack of efficacy may be the result of low potency or loss of activity during delivery because of autoxidation effects, as well as the potential for inactivation by pulmonary enzymes. GSH is subject to rapid autoxidation to the inactive GSSG form (Curello, S. et al., *Clin Chem,* 33:1448-49, 1987) and is hence pharmacologically unstable in the reduced form when aerosolized and inhaled (Carl White M. D., pers comm.), losing a large fraction of its activity by the time the target site in the airway is reached. In addition, γ-glutamyltransferase present at high concentrations in the pulmonary space readily degrades GSH to an inactive form (Corti et al., *Am J Resp Crit Care Med* 189:233-234, 2014), the abundance of which increases markedly upon GSH inhalation (Griese et al., *Am J Resp Crit Care Med* 188:83-89 Supplemental information, 2013). Improving thiol agents by combining disulfide-targeting with the superior pharmacology and specificity of biologic drugs is thus a key unmet therapeutic objective.

While the etiology of CF lung disease can be attributed to the altered rheological properties of mucus, compromised lung function is rarely evident at birth. Instead, bronchiectasis and airway obstruction progress with age of patient. This chronic lung injury results from a persistent cycle of bacterial infection and inflammatory response. Airway damage results when neutrophils recruited into the lung release matrix degrading enzymes, such as elastase, and harmful reactive oxygen species (reviewed in Konstan and Berger, *Pediatr Pulmonol* 24:137-142, 1997). Following persistent infection, interaction of mucins with DNA (Potter et al., *Am J Dis Child* 100:493-495, 1960; Lethem et al., *Am Rev Respir Dis* 100: 493-495, 1990; Lethem et al., *Eur Respir J* 3:19-23, 1990) and f-actin polymers (Sheils et al., *Am J Path* 148:919-927, 1996; Tomkiewicz et al., DNA and actin filament ultrastructure in cystic fibrosis sputum. In: *Cilia, mucus, and mucociliary interactions,* edited by Baum G L, Priel Z, Roth Y, Liron N, and Ostfeld E J. New York, N.Y.: Marcel Dekker, 1998) released from dying inflammatory cells may also occur, and can be responsible for some of the dense and viscous nature of CF sputum in severe disease. The inability to clear such mucus by cough or mucociliary clearance facilitates further colonization of the lung with opportunistic pathogens, airway remodeling, and eventually death.

Interventions designed to mitigate directly the consequences of CFTR defects therefore are particularly desirable, as these may prevent or attenuate disease progression. While direct correction of CF by gene therapy is not yet attainable, the use of potentiator and corrector therapies to restore some degree of CFTR function to defective proteins has been demonstrated recently (Sloane, P A and Rowe, S M, *Current Opinion in Pulmonary Medicine* 16: 591-7, 2010). Such therapy is limited to a small percentage of CF patients with a particular CFTR defect, such as the G551D mutation targeted by ivacaftor/Kalydeco™ (Jones, A M and Helm, J M, *Drugs* 69: 1903-10, 2009). However, in these few individuals dramatic results have been observed (Accurso, F J; Rowe, S M; Clancy, J P; Boyle, M P; Dunitz, J M; Durie, P R; Sagel, S D; Hornick, D B et al., *The New England Journal of Medicine* 363: 1991-2003, 2010) demonstrating that mechanistic intervention in CF is capable of mitigating late-stage consequences such as those resulting from chronic infection and inflammation. Currently, however, symptomatic rather than disease-modifying approaches including antibiotic regimens coupled with drugs that facilitate the clearance of purulent airway secretions remain the mainstay treatments for progressive airway disease. Inhalation of purified rhDNase (Pulmozyme™; Genentech, USA), which digests extracellular DNA present in the CF airway, is widely used as a respiratory decongestant. Such treatment is clinically effective for diminishing sputum viscosity and stabilizing the forced expiratory volume (FEV) (Fuchs et al., *N Engl J Med* 331:637-642, 1994). Other investigative therapies aimed at breaking down mucin or actin polymers, including N-acetylcysteine (NAC), nacystelyn (an N-acetyl-L-cysteine derivative), and gelsolin, can also reduce sputum viscosity experimentally, but have yet to demonstrate clinical efficacy and attain approval for treatment of CF in the United States (Nash, E F et al., *Cochrane Database of Systematic Reviews*, 2010(1):CD007168, 2009).

Other approaches being utilized to improve mucus clearance include mucoactive agents such as inhaled hypertonic saline and inhaled high-dose mannitol (Fahy, J. V. and Dickey, B. F., *N Engl J Med* 363:2233-47, 2010). These agents are thought to act by pulling water osmotically into the mucus layer to increase hydration, or to improve clearance through induction of coughing reflexes. Some evidence exists for both mechanisms (Levin, M. H. et al., *J Biol Chem* 281:25803-12, 2006; Boucher, R. C., *Trends Mol Med* 13:231-240, 2007). However, mucoactives are symptomatic treatments (not disease-modifying), and efficacy is generally only moderate as many patients are not able to tolerate the high doses that can have the greatest clinical effect (Aziz, I. and Kastelik, J. A., *N Engl J Med* 354:1848-1851, 2006).

Findings by White and colleagues (Rancourt et al., *Am J Physiol Lung Cell Mol Physiol* 286:L931-L938, 2004; Rancourt et al., *Free Radical Biol & Med* 42:1441-43, 2007) have found that the use of a protein or peptide containing a thioredoxin active site in the reduced state is useful for increasing the liquefaction of mucus or sputum in a patient that has excessively viscous or cohesive mucus or sputum, including a patient having CF, wherein the mucus or sputum is contacted with the protein or peptide (U.S. Pat. No. 7,195,766 and U.S. Pat. No. 7,534,438, both of which are incorporated herein by reference in their entirety). In this system (see FIG. 3), a transient mixed-disulfide between the N-terminal cysteine of the thioredoxin active site and a cysteine of a target protein (found in the mucus or sputum) is formed, followed immediately by nucleophilic attack on the intramolecular mixed disulfide linkage and release of oxidized thioredoxin and the fully-reduced target (Wynn et al., Biochemistry 34(37):11807-11813, 1995), thus allowing for re-formation of cysteine disulfides in the mucus or sputum but at the same time also allowing free access of reduced or oxidized thioredoxin to enter cells and induce undesired off-target activities following re-reduction by the endogenous thioredoxin reductase—NADPH system. In addition White and colleagues have shown reduced thioredoxin to mitigate the abnormal viscoelasticity of human CF mucus in vitro and in ex vivo animal implantation studies (Rancourt et al., *Free Radical Biol & Med* 42:1441-43, 2007), as well as to inhibit the activity of pro-inflammatory neutrophil elastase by disruption of active site disulfide bonds (Lee et al., *Am J Physiol Lung Cell Mol Physiol* 289:L875-L882, 2005). Compared to GSH and thiol agents such as NAC, thioredoxin is a more potent disulfide bond-reducing molecule and is much less susceptible to inactivation by autoxidation. Taken together, this creates the opportunity to restore a normal disulfide reduction state to mucus with a pharmacologically stable molecule. Such a therapy may prevent or delay the cascade of chronic infection, inflammation and lung function decline that leads to early death in CF patients. However, there is also a strong motivation to avoid the potential pro-inflammatory and other intracellular regulatory effects of thioredoxin (Arner, E. S. and A. Holmgren, *Eur J Biochem* 267: 6102-6109, 2000; Rancourt et al., *Free Radical Biol & Med* 42:1441-43, 2007) as well as to increase the potency of mucus viscosity-modulation by preventing mucin Cys re-oxidation. These improvements are the subject of the present invention.

SUMMARY OF THE INVENTION

One embodiment of the present invention relates to a method to decrease viscosity of mucus or sputum in a patient that has excessively viscous or cohesive mucus or sputum. The method includes the step of contacting the mucus or sputum of the patient with a composition comprising a protein or peptide containing a thioredoxin monocysteinic active site in a reduced state effective to decrease the viscosity of the mucus or sputum as compared to prior to the step of contacting. In one aspect of this embodiment, the patient has a lung disease in which abnormal or excessive viscosity or cohesiveness of mucus or sputum is a symptom or cause of the disease. In one aspect, the patient has a lung disease selected from, cystic fibrosis (CF), chronic obstructive pulmonary disease, bronchiectasis and asthma. In a preferred aspect, the patient has CF. In another aspect of this embodiment, the patient has a lung disease in which abnormal or excessive viscosity or cohesiveness of mucus or sputum is associated with a deficiency of biological reductant activity. In yet another aspect of this embodiment, the patient has a digestive tract disease associated with thickened or abnormal mucus, including but not limited to coccidiosis.

In one aspect, the step of contacting the mucus or sputum of the patient with the composition is performed by introducing the composition to the patient by a route selected from nasal, intratracheal, bronchial, direct installation into the lung, inhaled and oral. In one aspect, the mucus or sputum to be contacted is located in the respiratory tract, the digestive tract (i.e. gastrointestinal tract) or the reproductive tract of the patient.

In another aspect, the composition is administered to the patient in a pharmaceutically acceptable carrier.

In any of the foregoing aspects, the step of contacting the mucus or sputum of the patient with the composition increases the percentage of free thiols in a sample of mucus or sputum from the patient as compared to prior contact with the composition.

In any of the foregoing aspects, after the step of contacting the mucus or sputum of the patient with the composition the patient has at least about a 2.5% increase in forced expiratory volume (FEV) as compared to prior to the step of contacting.

In any of the foregoing aspects, the thioredoxin monocysteinic active site comprises an amino acid sequence selected from C-X-X-S (SEQ ID NO:24), C-X-X-X (SEQ ID NO:17), X-C-X-X-X-X (SEQ ID NO:19), X-C-G-P-X-X (SEQ ID NO:21), W-C-G-P-X-K (SEQ ID NO:23), X-C-X-X-S-X (SEQ ID NO:25), X-C-G-P-S-X (SEQ ID NO:26), or W-C-G-P-S-K (SEQ ID NO:27) wherein the C residue is in a reduced state, and wherein the X residues are any amino acid residue other than cysteine. In a preferred aspect, the thioredoxin monocysteinic active site comprises the amino acid sequence C-X-X-S (SEQ ID NO:24) as described above.

In any of the above aspects, the protein having a thioredoxin monocysteinic active site comprises thioredoxin selected from the group consisting of prokaryotic thioredoxin, fungal thioredoxin, plant thioredoxin, and mammalian thioredoxin. In a preferred aspect, the protein comprises human thioredoxin.

In any of the above aspects of the invention, the composition further comprises a reducing agent for reducing the thioredoxin monocysteinic active site of the protein. In a further aspect, the composition comprises thioredoxin reductase and NADH or NADPH.

Another embodiment of the invention relates to a composition for use in decreasing viscosity of mucus or sputum, comprising a protein or peptide containing a thioredoxin monocysteinic active site in a reduced state and at least one additional agent for treatment of excessively viscous or cohesive mucus or sputum. In one aspect of this embodiment, the thioredoxin monocysteinic active site comprises an amino acid sequence selected from C-X-X-S (SEQ ID NO:24), C-X-

X-X (SEQ ID NO:17), X-C-X-X-X-X (SEQ ID NO:19), X-C-G-P-X-X (SEQ ID NO:21), W-C-G-P-X-K (SEQ ID NO:23), X-C-X-X-S-X (SEQ ID NO:25), X-C-G-P-S-X (SEQ ID NO:26), or W-C-G-P-S-K (SEQ ID NO:27) wherein the C residue is in a reduced state, and wherein the X residues are any amino acid residue other than cysteine. In a preferred aspect, the thioredoxin monocysteinic active site comprises the amino acid sequence C-X-X-S (SEQ ID NO:24) as described above. In any of the foregoing aspects for this embodiment, the protein having a thioredoxin monocysteinic active site comprises thioredoxin selected from a group consisting of prokaryotic thioredoxin, fugal thioredoxin, plant thioredoxin, and mammalian thioredoxin. In one aspect, the protein comprises human thioredoxin.

Still further, in any one of the foregoing aspects of this embodiment, the composition comprises a reducing agent. In still a further aspect, the composition further comprises thioredoxin reductase and NADH or NADPH.

Yet another embodiment of the present invention relates to a pharmaceutical composition comprising a protein or peptide containing a thioredoxin monocysteinic active site in a reduced state. In one aspect, the composition is formulated for aerosol administration to the lung. In still another aspect, the composition is formulated for oral administration. In any of the foregoing aspects for this embodiment, the thioredoxin monocysteinic active site comprises an amino acid sequence selected from C-X-X-S (SEQ ID NO: 24), C-X-X-X (SEQ ID NO:17), X-C-X-X-X-X (SEQ ID NO: 19), X-C-G-P-X-X (SEQ ID NO:21), W-C-G-P-X-K (SEQ ID NO:23), X-C-X-X-S-X (SEQ ID NO:25), X-C-G-P-S-X (SEQ ID NO:26), and W-C-G-P-S-K (SEQ ID NO:27), wherein the C residue is in a reduced state, and wherein the X residues are any amino acid residue other than cysteine. In still another aspect, the pharmaceutical composition is formulated for aerosol administration to the lung by a nebulizer device. In one aspect, the nebulizer device is a vibrating-mesh nebulizer. In another aspect, the pharmaceutical composition further comprises a reducing agent. In any of the foregoing aspects of this invention, the pharmaceutical composition further comprises thioredoxin reductase and NADH or NADPH.

Yet another embodiment of the present invention relates to a composition comprising a protein or peptide containing a thioredoxin monocysteinic active site, wherein the cysteine in the monocysteinic active site is covalently bound to a cysteine residue in a mucus protein. In one aspect, the thioredoxin monocysteinic active site comprises an amino acid sequence selected from C-X-X-S (SEQ ID NO: 24), C-X-X-X (SEQ ID NO:17), X-C-X-X-X-X (SEQ ID NO: 19), X-C-G-P-X-X (SEQ ID NO:21), W-C-G-P-X-K (SEQ ID NO:23), X-C-X-X-S-X (SEQ ID NO:25), X-C-G-P-S-X (SEQ ID NO:26), and W-C-G-P-S-K (SEQ ID NO:27), wherein the C residue is in a reduced state, and wherein the X residues are any amino acid residue other than cysteine. In any one of the above aspects, the mucus protein is a respiratory mucus protein or a digestive tract mucus protein. In another aspect, the mucus protein is a mucin.

Another embodiment of the present invention relates to a method to decrease viscosity of mucus or sputum in a patient that has excessively viscous or cohesive mucus or sputum. The method includes the step of contacting the mucus or sputum of the patient with a composition comprising a disulfide bond reducing agent and a cysteine-blocking agent. In one aspect, the disulfide bond reducing agent and a cysteine-blocking agent are the same molecule. In a further aspect, the same molecule is a protein or peptide containing a thioredoxin monocysteinic active site. In yet another aspect, the disulfide bond reducing agent and the cysteine-blocking agent are different molecules. In still another aspect, the disulfide bond reducing agent can be dithiothreitol (DTT), ethylenediaminetetraacetic acid (EDTA), glutathione, dithioglycolic acid, 2-mercaptoethanol, N-acetyl cysteine or Tris-(2-carboxyethyl)phosphene. In yet a further aspect, the cysteine-blocking agent can be iodoacetamide, iodoacetic acid, or other alkylation agents.

Yet another embodiment of the present invention relates to a method to treat a patient having excessively viscous or cohesive mucus. The method includes the step of administering to the patient a composition comprising a compound having a thioredoxin active site that is incapable of cellular uptake. In one aspect, the compound can be a protein or peptide comprising a thioredoxin monocysteinic active site, a fusion protein comprising a thioredoxin portion and a cell surface receptor ligand portion, or a combination of a protein or peptide comprising a thioredoxin active site and a blocking compound for the cysteine corresponding to the cysteine at position 35 of SEQ ID NO:12.

Another embodiment of the present invention relates to a method of preventing systemic exposure to a drug substance in a patient. The method includes the step of administering the drug to the patient by a delivery route including but not limited to a pulmonary, oral or topical delivery route. In yet another aspect, the drug forms a covalent bond to its target site once administered. In still another aspect, the drug substance is a thiol-containing drug and can be, for example, a protein or peptide containing a thioredoxin monocysteinic active site in a reduced state. In still another aspect the drug substance is an antibiotic or anti-infective agent and is fused or attached by linker to a thioredoxin monocysteinic active site in a reduced state. In still another aspect the drug substance is an anti-inflammatory agent and is fused or attached by linker to a thioredoxin monocysteinic active site in a reduced state. In still another aspect the drug substance is a nucleic acid-hydrolyzing agent and is fused or attached by linker to a thioredoxin monocysteinic active site in a reduced state. In still another aspect the drug substance is a chemotherapeutic agent and is fused or attached by linker to a thioredoxin monocysteinic active site in a reduced state.

Still another embodiment of the present invention relates to a pharmaceutical composition comprising a protein or peptide containing a thioredoxin monocysteinic active site in a reduced state and further comprising at least one saccharide or saccharide derivative capable of stabilizing the reduced redox-active thiol group. In one aspect, the saccharide or saccharide derivative can be sucrose, sucralose, lactose, trehalose, maltose, galactose, raffinose, mannose or mannitol. In one aspect, the thioredoxin monocysteinic active site comprises an amino acid sequence selected from C-X-X-S (SEQ ID NO: 24), C-X-X-X (SEQ ID NO:17), X-C-X-X-X-X (SEQ ID NO: 19), X-C-G-P-X-X (SEQ ID NO:21), W-C-G-P-X-K (SEQ ID NO:23), X-C-X-X-S-X (SEQ ID NO:25), X-C-G-P-S-X (SEQ ID NO:26), and W-C-G-P-S-K (SEQ ID NO:27), wherein the C residue is in a reduced state, and wherein the X residues are any amino acid residue other than cysteine.

Another embodiment of the present invention relates to an animal feed composition comprising a protein or peptide containing a thioredoxin monocysteinic active site in a reduced state. In one aspect, the thioredoxin monocysteinic active site comprises an amino acid sequence selected from C-X-X-S (SEQ ID NO: 24), C-X-X-X (SEQ ID NO:17), X-C-X-X-X-X (SEQ ID NO: 19), X-C-G-P-X-X (SEQ ID NO:21), W-C-G-P-X-K (SEQ ID NO:23), X-C-X-X-S-X (SEQ ID NO:25), X-C-G-P-S-X (SEQ ID NO:26), and W-C-

G-P-S-K (SEQ ID NO:27), wherein the C residue is in a reduced state, and wherein the X residues are any amino acid residue other than cysteine.

In one aspect of any of the embodiments of the present invention, the patient is a vertebrate, including but not limited to mammals and birds. In still another aspect, the patient is a human. In yet another aspect, the patient is a chicken or a turkey.

Yet another embodiment of the present invention relates to a use of a composition comprising a protein or peptide containing a thioredoxin monocysteinic active site in a reduced state to decrease viscosity of mucus or sputum in a patient that has excessively viscous or cohesive mucus or sputum, wherein contacting the mucus or sputum of the patient with the composition decreases the viscosity of the mucus or sputum as compared to prior to the step of contacting. In one aspect, the thioredoxin monocysteinic active site comprises an amino acid sequence selected from C-X-X-S (SEQ ID NO: 24), C-X-X-X (SEQ ID NO:17), X-C-X-X-X-X (SEQ ID NO: 19), X-C-G-P-X-X (SEQ ID NO:21), W-C-G-P-X-K (SEQ ID NO:23), X-C-X-X-S-X (SEQ ID NO:25), X-C-G-P-S-X (SEQ ID NO:26), and W-C-G-P-S-K (SEQ ID NO:27) wherein the C residue is in a reduced state, and wherein the X residues are any amino acid residue other than cysteine.

BRIEF DESCRIPTION OF THE DRAWINGS

FIGS. 1a-1b shows the enzymatic activity of a protein or peptide containing a thioredoxin monocysteinic active site (referred to as r(Cys)hTrx) compared with a protein or peptide containing a wild-type thioredoxin active site (referred to as WTrhTrx). FIG. 1a shows non-specific 5,5'-dithiobis-(2-nitrobenzoic acid) (DTNB or Ellman's reagent) reduction reflects loss of 1 reducible cysteine in thioredoxin monocysteinic active site vs. wild-type. FIG. 1b shows that a protein or peptide containing a thioredoxin monocysteinic active site (r(Cys)hTrx) had similar or greater potency vs. a protein or peptide containing a wild-type thioredoxin active site (WTrhTrx) in a human sputum compaction assay at concentration amounts of 12.5 µM, 25 µM and 50 µM.

As shown in FIG. 3, steps I and II show the formation of a transient mixed-disulfide between the N-terminal Cys (located at position 32 in the human TRX-1 amino acid sequence) of the Trx active site and one Cys of the target protein disulfide, followed by step III. Step III shows the nucleophilic attack on the intermolecular mixed disulfide bond by the C-terminal Cys of the Trx active site, located at position 35 in the human TRX-1 amino acid sequence. This second reduction resolves the mixed-disulfide linkage and releases oxidized Trx and the fully-reduced target. By mutating the C-terminal active site Cys residue at position 35 of Trx to a non-cysteine amino acid, such as a serine residue (a monocysteinic variant), or otherwise modifying the protein sequence such as to interfere with the nucleophilic attack by the C-terminal active site Cys at position 35, thioredoxin is still able to function as a reducing agent, but unlike the wild-type enzyme such monocysteinic active site variants remain covalently attached to the reduced target protein via the unresolved intermolecular mixed-disulfide linkage.

DETAILED DESCRIPTION OF THE INVENTION

Figure 2:
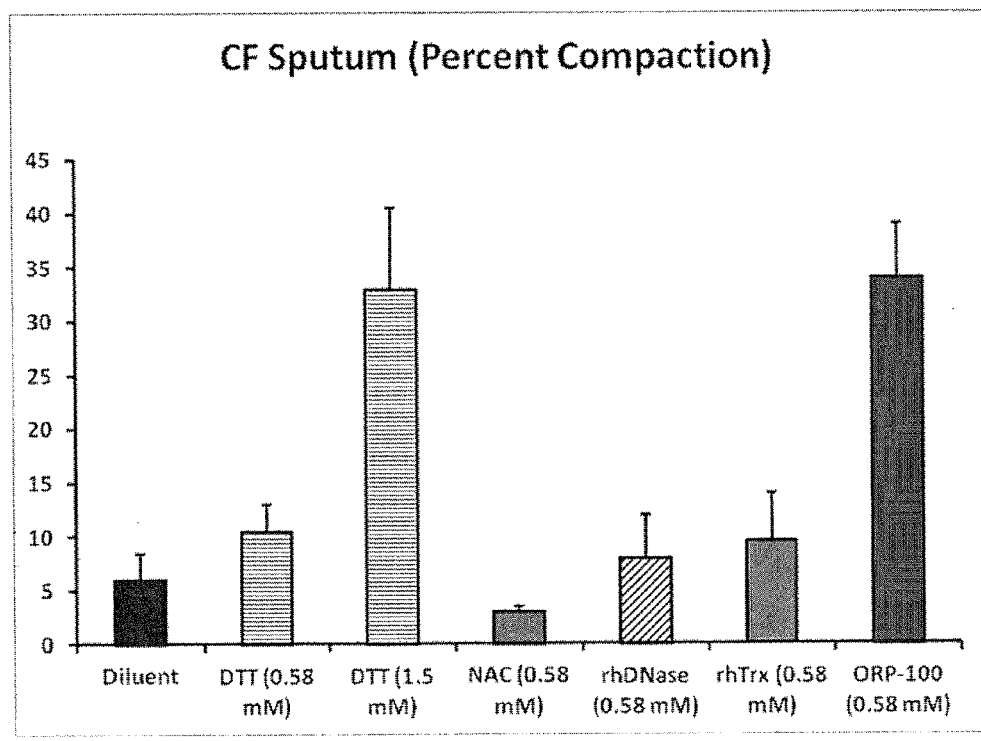
FIG. 2 shows the effect of wildtype rhTrx, r(Cys)hTrx and various controls including dithiothreitol (DTT) at two concentrations (0.58 mM and 1.5 mM), N-acetyl cysteine (NAC) and recombinant human DNase (rhDNase) at equimolar concentrations on normalization of patient sputum samples (n=6 per treatment) in a sputum-compaction assay.
Figure 3:
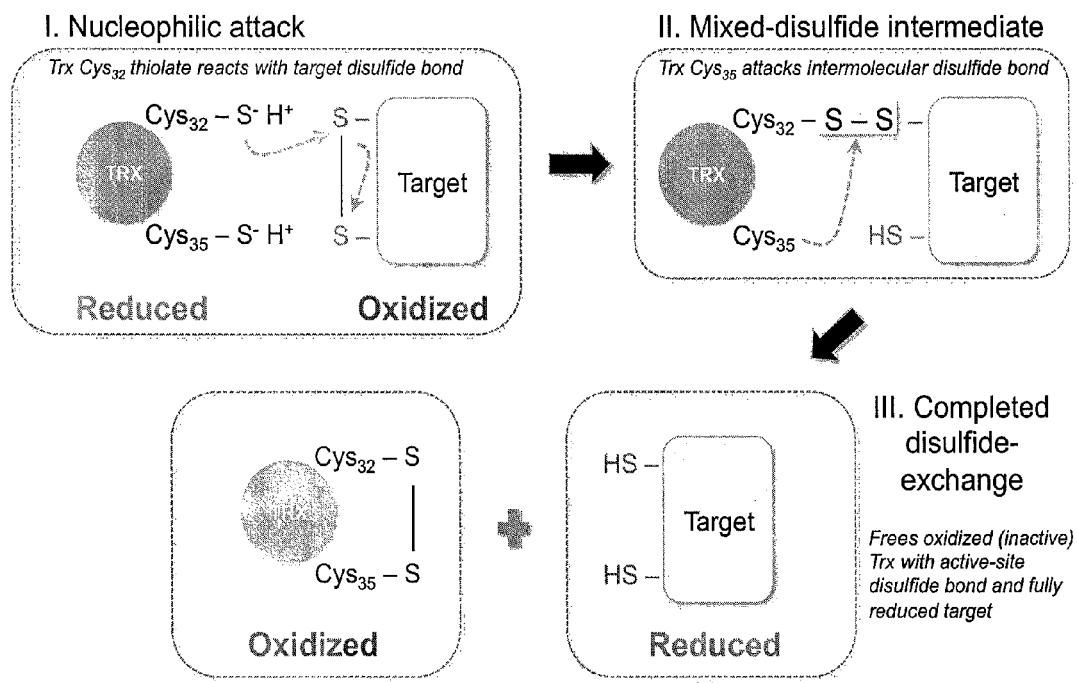
FIG. 3 illustrates the mechanism of disulfide bond formation with a protein or peptide having a thioredoxin monocysteinic active site at position 35 of SEQ ID NO:12. The mechanism of native Trx disulfide-reduction involves a two-step reaction.

The present invention generally relates to the use of a protein or peptide containing a thioredoxin monocysteinic active site in a reduced state to induce, enhance and/or increase the liquefaction of mucus or sputum. More specifically, the present inventor has discovered that proteins or peptides with a monocysteinic thioredoxin active site decrease the viscosity and/or cohesiveness of sputum or mucus and thereby are effective agents for enhancing or increasing the liquefaction of sputum or mucus. Accordingly, proteins or peptides containing a monocysteinic thioredoxin active site in reduced state, or nucleic acid molecules encoding such proteins, can be used alone or in a composition to treat a variety of conditions or diseases associated with undesirable mucus or tenacious and viscous sputum. For example, respiratory diseases such as cystic fibrosis, chronic obstructive pulmonary disease, bronchiectasis and asthma are particularly amenable to treatment using the product and process of the invention. Also, digestive tract diseases associated with thickened or adherent mucus such as coccidiosis are also particularly amenable to treatment using the product and process of the invention. Therefore, the present invention relates to the use of proteins containing a monocysteinic active site of thioredoxin in a reduced state for decreasing the viscosity of mucus or sputum, particularly mucus or sputum that is abnormally or excessively viscous and/or cohesive. The proteins are administered to a patient that is suffering from or affected by such abnormal or excessive mucus or sputum in a manner and amount effective to decrease the viscosity of the mucus or sputum and preferably, to provide a therapeutic benefit to the patient.

Thioredoxin and proteins containing either the wild-type (or native) thioredoxin active site (also referred to herein as "rhTxr") or containing the thioredoxin monocysteinic active site (also referred to herein as "r(Cys)hTrx") have advantages over other reducing agents for use in the treatment of conditions such as cystic fibrosis. For example, unlike other reducing agents such as N-acetylcysteine (NAC), Nacystelyn (NAL), dithiothreitol (DTT), or reducted glutathione (GSH), thioredoxin is less susceptible to inactivation by enzymatic or auto-oxidative mechanisms, including reactions to produce superoxide, hydrogen peroxide, hydroxyl radical and other toxic oxygen metabolites. Furthermore, native or wildtype thioredoxin is a naturally-occurring compound which is normally secreted extracellularly onto the airway surface, and therefore, introduction of thioredoxin into the airway should be non-irritating and unlikely to induce an immune response. Thioredoxin is also not glycosylated, and as such, it is more easily manufactured, and administration of the protein in natural or recombinant form should not induce an innate immune response. Perhaps even more significantly, reduced thioredoxin, in contrast to other reducing agents, more rapidly and potently restores the treated mucus or sputum to a normal viscosity level, and this normalization lasts for a longer duration. NAC, NAL, DTT, and GSH, for example, become "spent" or oxidized over time and at this stage, normalized sputum or mucus can revert back to an abnormal viscosity state. In contrast, the decrease in viscosity produced by thioredoxin appears to endure longer, most likely due to its cyclic re-reduction by its reducing system. Further, by remaining covalently bound to mucin Cys residues r(Cys)hTrx creates an even more potent and longer-duration reduction in viscosity vs native rhTrx. Finally, thioredoxin is both more potent and more specific for disulfide bond-reduction than other reducing agents and therefore, it can be used at significantly lower doses than other agents to achieve a beneficial effect.

In addition to the above-described advantages, thioredoxin has other benefits which increase its usefulness in disease conditions. For example, it is known that thioredoxin induces MnSOD (e.g., see U.S. Pat. No. 5,985,261 to White et al., incorporated herein by reference in its entirety) which is predicted to decrease the toxicity of certain bacterial toxins (including, but not limited to, endotoxin from bacterial cell walls of gram-negative bacteria, pyocyanin from *Pseudomonas aeruginosa*, and others) in disease sputum (e.g., cystic fibrosis sputum). In addition, thioredoxin has extracellular anti-inflammatory properties (Lee, R. L., et al., *Am J Physiol Lung Cell Mol Physiol,* 289(5):L875-82, 2005) that can enhance the overall treatment of a respiratory condition.

Thioredoxin (Trx) is a protein disulfide reductase that catalyzes numerous thiol-dependent cellular reductive processes. Native thioredoxin contains two redox-active cysteines that are highly conserved across species. In their oxidized form, these cysteines form a disulfide bridge that protrudes from the three dimensional structure of the protein (Holmgren, *Annu Rev Biochem* 54:237-271, 1985). Reduction of this active center by the NADPH-dependent thioredoxin reductase (TR) enzyme allows Trx to function as an electron carrier with dithiol/disulfide exchange capability (Oblong et al., *Biochemistry* 32:7271-7277, 1993). Protein disulfides are a preferred substrate for Trx-mediated reducing action. Modification of the Trx C-terminal active site cysteine produces a monocysteinic active site, which as discussed below, has substantial advantages over Trx having the native or wildtype active site. The persistent and viscous nature of airway secretions in cystic fibrosis disease leads to airway obstruction, opportunistic infection, and deterioration of lung function. Recognizing that respiratory mucins contain multiple cysteine domains that are believed to play an essential role in polymerization (Bell et al., *Biochem J* 357:203-209, 2001; Asker et al., *Biochem J* 333:381-387, 1998) as well as increasing the entanglement of mucins via numerous intramolecular disulfide bonds, the present inventor sought to determine whether Trx containing a monocysteinic active site could serve as an effective mucus viscosity modulator by reduction of mucin disulfides.

There are several advantages and benefits of thioredoxin containing a monocysteinic active site versus thioredoxin containing the native or wildtype active site. The monocysteinic modification is designed to minimize potential side effects of thioredoxin associated with intracellular signaling or systemic exposure such as those described by Rancourt et al. (*Free Radical Biol & Med* 42:1441-43, 2007). This modification prevents nucleophilic attack on the mixed disulfide formed between thioredoxin and a target protein disulfide that is catalyzed by the N-terminal thioredoxin active site cysteine (for example located at position 32 in human thioredoxin, SEQ ID NO:14). Surprisingly, the present inventor has determined that the thioredoxin containing a monocysteinic active site has greater potency than wild-type thioredoxin decreasing (trending toward liquefying) and normalizing the viscosity of diseased human mucus. Even though thioredoxin containing the monocysteinic active site logically would be expected to have less reducing potential due to the gross perturbation caused by loss of an active site cysteine and therefore following an initial catalytic reaction at the N-terminal thioredoxin active site cysteine, be bound covalently to mucus proteins (such as the heavily disulfide-bonded mucins MUC5AC and MUC5B) and would be unable to be reduced and perform repeated catalysis, the present inventor has found that not only does the thioredoxin containing the monocysteinic active site not show impaired activity compared to wild-type thioredoxin, it exhibits greater quantitative ability to reduce human CF mucus viscosity in a rheological assay. Based on this unexpected result, the inventor has concluded that the enhanced potency of thioredoxin containing the monocysteinic active site must be a consequence of the covalently-linked thioredoxin and mucus functioning to block re-formation of cysteine disulfides in mucins, thus providing an exceedingly durable and long-lived change in mucin oligomer gel structure and pore size. At the same time, covalent linkage of a thioredoxin containing the monocysteinic active site to its mucin target sequesters and hence prevents cellular uptake and internalization of inhaled thioredoxin, which has the duel benefits of preventing off-target effects due to undesired thioredoxin activity within cells, while at the same time facilitating clearance of mucus-linked spent drug from the body. As the only therapeutic use envisioned previously in the art for Cys-modified monocysteinic thioredoxins is to facilitate uptake of non-reduced forms via lipid rafts in endothelial cells following injection into the systemic circulation (Hara et al., *Antiox Redox Sig* 9:1427-37, 2007; Kondo et al., *Antiox Redox Sig* 9:1439-48, 2007; US Patent Applications 20080119398, 20090075871, and 20100184215), and thus teaching away from the present invention which is focused on preventing systemic exposure and intracellular uptake, the extracellular mechanism for enhanced potency and safety of monocysteinic active site thioredoxin in a reduced form is unanticipated and highly novel.

Mucus obstruction of the airways can cause significant morbidity and mortality in patients with CF. The present inventor has demonstrated that the viscoelastic properties facilitating the persistence of these secretions within airways are markedly diminished by Trx containing a monocysteinic active site. This conclusion is supported by two lines of experimental evidence. First, compaction assay results indicate that large amounts of liquid are released from the gel matrix of CF sputum during incubation with monocysteinic Trx. Occurring simultaneously with this release are decreases in the volume of solid matter, indicating that the gel forming constituents of sputum were being solubilized. This normalization of CF sputum viscosity could often be observed grossly in CF sputum samples during the incubation period, and therefore, is not an artifact of centrifugal disruption. The liberation of liquid by monocysteinic Trx is expected to have important therapeutic implications since restoration of water volume at airway surfaces can restore the mucociliary transport ability of CF epithelium (Jiang et al., *Science* 262:424-427, 1993) and relief of excess viscosity will, based on the Button et al. (*Science,* 2012) gel-on-brush model, allow hydration of the underlying periciliary layer and restore mucociliary transport, the loss of which is the primary cause of pathology in CF. Second, magnetic microrheometry measurements provide direct evidence that sputum viscoelasticity declines as a result of reduction of sputum components by monocysteinic Trx.

CF sputum is a non-Newtonian fluid exhibiting both liquid and solid characteristics. Polymers when present in solutions at low concentration are able to rotate freely. When polymers become concentrated or cross-linked to such a degree that their rotation is hindered, a solution has reached a transition phase called the percolation threshold (Forgacs, *J Cell Sci* 108:2131-2143, 1995). At the percolation threshold the solution begins to acquire characteristics of a solid, and the elastic moduli continue to increase as more cross-polymer interactions are added, until each filament in the sample is incorporated into the matrix. Biochemical analyses have revealed that mucins MUC5AC and MUC5B, secreted by cells lining the respiratory tract, are the major gel forming polymers components of airway mucus (Hovenberg et al., *Glycoconj J* 13:839-847, 1996; Thornton et al., *Biochem J* 316:967-975, 1996; Thornton et al., *J Biol Chem* 272:9561-9566, 1997). Cysteine domains present on these mucins contribute to polymer formation, and possibly interaction with neighboring mucin chains, by intramolecular disulfide bond formation (Bell et al., *Biochem J* 357:203-209, 2001; Asker et al., *Biochem J* 333:381-387, 1998) which is a likely contributor to gel mesh entanglement. Since disulfide bonds on proteins are the preferred substrates for Trx enzymatic activity, mucin polymers are targets for reduction during the liquefaction of sputum by Trx. This is supported by PAS staining which reveals changes in the solubility of high molecular weight glycoforms in Trx-treated sputum. Detection of greater concentrations of glycoproteins in the liquid phase of Trx-exposed sputum was further indicated by a more intense yellow color and had greater opacity than liquid phase derived from diluent-treated samples. The enhanced electrophoretic mobility of PAS-detectable glycoproteins in Trx-exposed sputum also suggests that these macromolecules may decrease in size during enzymatic reduction. Findings from this electrophoretic analysis are in agreement with compaction assay measurements by demonstrating that glycoprotein release into liquid phase coincides with the decrease in mass of the gel matrix during exposure to Trx, as well as the observation of increased labeling of free thiols in sputum following Trx treatment (Rancourt, R. et al., *Free Radic Biol Med,* 42(9):1441-1453, 2007).

Once chronic effects of inflammation and infection have established in a CF patient, neutrophil lysis within the airways of diseased CF lungs results in the deposition of extracellular DNA into airway secretions (Lethem et al., *Eur Respir J* 3:19-23, 1990). By non-covalent interactions, this DNA becomes entangled within mucin glycoproteins, increasing mucus gel viscoelasticity (Sachdev et al., *Chest* 81:41 S-43S, 1982). DNA present in sputum becomes increasingly soluble following Trx treatment. A logical explanation is that Trx activity causes structural changes within the gel matrix which are sufficient to relieve entanglement interactions between DNA and the affected macromolecules. It is uncertain what the relative contribution of this increased DNA solubility has toward viscoelastic changes observed during exposure of CF sputum to Trx. Nonetheless, from a clinical standpoint, loosening or removal of DNA from the insoluble gel phase of sputum could render it more susceptible to DNase activity during such treatment in CF. In addition, the action of monocysteinic r(Cys)hTrx to reduce mucus viscosity and prevent rapid re-formation of disulfide bonds on mucin cysteines will function to create a more permeable, accessible mucus layer as well as de-bulking accumulated mucus plugs. These actions are expected to facilitate access of other therapeutics to the deep lung and the pulmonary epithelial surface. Therefore, the mechanistic method of the invention has a strong potential for synergy with existing symptomatic therapies for CF and other obstructive pulmonary diseases such as delivery of inhaled antibiotics, mucoactive substances or mucolytic DNA-hydrolyzing agents.

Trx containing a monocysteinic active site has both higher activity and greater oxidative stability than reduced glutathione and acts extracellularly in the airway mucus and does not enter lung cells. Trx comprising a monocysteinic active site decreases viscosity, increases the liquid fraction and diminishes the viscoelasticity of sputum, for example in CF sputum. The development of mucus-reducing systems that stimulate release of liquid, and reduce the viscosity of airway secretions, is expected to have therapeutic potential for diseases such as CF, as well as for the treatment of excessive or abnormal mucus viscosity and/or cohesiveness that may be associated with other respiratory conditions (e.g., chronic or acute bronchitis; bronchiectasis; COPD/emphysema; asthma; acute tracheitis; acute or chronic sinusitis; atelectasis resulting from acute or chronic mucus plugging of the airways; bronchiolitis) or with various digestive disorders (i.e., gastrointestinal), such as coccidiosis or reproductive disorders associated with or exacerbated by excessive or abnormal mucus viscosity and/or cohesiveness (e.g., acute, subacute or chronic bowel obstruction due to mucus inspissation; infertility due to obstruction of vital reproductive structures). Since Trx containing a monocysteinic active site in a reduced state becomes covalently linked to mucin once it reacts with mucin disulfide bonds, such a mechanism of action will also facilitate clearance of spent (oxidized) drug along with mucus, may prevent or attenuate cellular update and thioredoxin-mediated redox signaling, and may prevent or attenuate presentation to immune cells.

Accordingly, one embodiment of the present invention relates to a method to normalize and decrease the viscosity of mucus or sputum in a patient that has excessively viscous or cohesive mucus or sputum. The method includes the step of contacting the mucus or sputum of the patient with a composition comprising a protein or peptide containing a thioredoxin monocysteinic active site in a reduced state. The protein is effective to decrease the viscosity of the mucus or sputum as compared to prior to the step of contacting.

According to the present invention, the term "mucus" generally refers to a usually clear viscid fluid that is secreted by mucous membranes in various tissues of the body, including by the respiratory, gastrointestinal, and reproductive tracts. Mucus moistens, lubricates and protects the tissues from which it is secreted. It comprises mucin macromolecules (including mucus proteins, nucleic acids and carbohydrates), which are the gel-forming constituents of mucus. Mucus proteins include but are not limited to respiratory mucus proteins and digestive tract mucus proteins. The viscoelastic properties of normal mucus are dependent on the concentration, molecular weight, and degree of entanglement between mucin polymers. The term "sputum" generally refers to a mixture of saliva and discharge from the respiratory passages, including mucus. Sputum is typically an expectorated mixture of saliva and mucus (and other discharge from the respiratory tissues). Therefore, mucus is a primary component of sputum, and as such, the presence of excessively viscous mucus results in a sputum which is itself excessively viscous. The present invention relates to decreasing the viscosity of the mucus or sputum. The term "liquefaction" refers to the act of becoming more liquid. Therefore, an increase in the liquefaction of mucus or sputum refers to the increase in liquid phase or liquid state of mucus or sputum, as compared to a more solid or viscous phase. In the case of abnormally viscous or excessive mucus associated with disease, the objective is to restore a normal level of mucus viscosity. Hence, liquefaction may also be considered as a reduction in mucus viscosity.

It is appreciated that normal mucus function is achieved by having the appropriate ratio of biological reductants to oxidizable cysteines. Hence, a deficiency of biological reductant activity is therefore caused by either an excess of oxidizable cysteines or a lack of biological reductants.

The general functions of mucus and sputum in the body require that the mucus (and thus the mucus component of the sputum) have viscoelastic properties. In an individual with normal mucus and sputum (i.e., a healthy individual, or more particularly, an individual who does not suffer from symptoms or a condition caused or exacerbated by the viscosity or cohesiveness of mucus or sputum), the viscoelasticity is dependent on the concentration, molecular weight, and entanglements between mucin polymers (Verdugo et al., *Biorheology* 20:223-230, 1983). Especially in CF, when mucins in the mucus interact with DNA (Potter et al., *Am J Dis Child* 100:493-495, 1960; Lethem et al., *Am Rev Respir Dis* 100:493-495, 1990; Lethem et al., *Eur Respir J* 3:19-23, 1990) and f-actin polymers (Sheils et al., *Am J Path* 148:919-927, 1996; Tomkiewicz et al., DNA and actin filament ultrastructure in cystic fibrosis sputum. In: *Cilia, mucus, and mucociliary interactions*, edited by Baum G L, Priel Z, Roth Y, Liron N, and Ostfeld E J. New York, N.Y.: Marcel Dekker, 1998) released from dying inflammatory cells, the mucus (and thus sputum) can additionally become even more dense and viscous. The inability to clear abnormal, thickened mucus by cough or mucociliary clearance facilitates colonization of the lung with opportunistic pathogens. Therefore, abnormally or excessively viscous and/or cohesive mucus is characterized as mucus that is measurably or detectably more viscous or cohesive than mucus from a normal or healthy patient (preferably an age and sex-matched patient), and/or as mucus which, by virtue of its level of viscosity and/or cohesiveness, causes or contributes to at least one symptom in a patient that causes discomfort or pain to the patient, or that causes or exacerbates a condition or disease. In other words, abnormally or excessively viscous and/or cohesive sputum is a deviation from normal mucus or sputum wherein it is desirable to treat the patient to provide some relief from the condition or other therapeutic benefit.

The method and composition of the present invention can be used to treat any patient in whom it is desirable to decrease the viscosity of mucus or sputum. In particular, patients that have certain lung, sinus, nasal, digestive or gastrointestinal, or reproductive diseases or conditions can benefit from treatment using the method of the present invention. The present invention is most useful for ameliorating or reducing at least one symptom of a condition or disease that is caused by or exacerbated by abnormal or excessive viscosity and/or cohesiveness of the mucus or sputum, which of course can include lung-associated diseases such as cystic fibrosis, as well as digestive diseases, such as coccidiosis. Other diseases may, at least some of the time, be associated with abnormal or excessive viscosity and/or cohesiveness of the mucus or sputum, and when such a symptom occurs, the method of the present invention can be used to decrease viscosity of the mucus or sputum and provide at least some relief or therapeutic benefit to the patient. Examples of such diseases include, but are not limited to: cystic fibrosis; chronic or acute bronchitis; bronchiectasis (non-CF and CF bronchiectasis); COPD/emphysema; acute tracheitis (bacterial, viral, mycoplasmal or caused by other organisms); acute or chronic sinusitis; atelectasis (lung or lobar collapse) resulting from acute or chronic mucus plugging of the airways (sometimes seen in a variety of diseases such as asthma); bronchiolitis (viral or other); acute, subacute or chronic bowel obstruction due to mucus inspissation including, but not limited to meconium ileus or meconium ileus equivalent in CF or similar disorders; other digestive diseases and infertility due to obstruction of (but not limited to) the cervix, seminal ducts or other vital reproductive structures. In addition, as improved mucociliary clearance is associated with clearance of bacteria and other pathogens from the lung, the composition and method of the present invention may be useful for reducing symptoms associated with excessive viscosity and/or cohesiveness of the mucus or sputum in patients with a variety of respiratory infections, including both viral and bacterial infections.

As such, a therapeutic benefit is not necessarily a cure for a particular disease or condition, but rather, preferably encompasses a result which most typically includes alleviation of the disease or condition, elimination of the disease or condition, reduction or elimination of a symptom associated with the disease or condition, prevention or alleviation of a secondary disease or condition resulting from the occurrence of a primary disease or condition (e.g., infectious disease caused by opportunistic pathogenic microorganisms that take advantage of the excessively viscous mucus in the respiratory tract), and/or prevention of the underlying disease or condition, or a symptom associated with the disease or condition. As used herein, the phrase "protected from a disease" refers to reducing the symptoms of the disease; palliative therapy (relieving or soothing a symptom of the disease without effecting a cure); reducing the occurrence of the disease, and/or reducing the severity of the disease or to alleviate disease at least one symptom, sign or cause of the disease or condition. Preventing refers to the ability of a composition of the present invention, when administered to a patient, to prevent a disease from occurring. Curing (or disease-modifying) refers to the ability of a composition of the present invention, when administered to a patient to cure the disease. To protect a patient from a disease includes treating a patient that has a disease (therapeutic treatment). Preventing a disease/condition includes preventing disease occurrence (prophylactic treatment). In particular, protecting a patient from a disease (or preventing disease) is accomplished by increasing (normalizing) the liquefaction of an abnormally viscous mucus or sputum in the patient by contacting the mucus or sputum with a protein or peptide comprising a thioredoxin monocysteinic active site in a reduced state such that a beneficial effect is obtained. A beneficial effect can easily be assessed by one of ordinary skill in the art and/or by a trained clinician who is treating the patient. The term "disease" refers to any deviation from the normal health of a patient and includes a state when disease symptoms are present, as well as conditions in which a deviation (e.g., infection, gene mutation, genetic defect, etc.) has occurred, but symptoms are not yet manifested.

Contact of the mucus and/or sputum of a patient with the protein or peptide comprising a thioredoxin monocysteinic active site in a reduced state (or compositions comprising such a protein) is intended to result in decreased viscosity/increased liquefaction of the mucus or sputum as compared to prior to contact with the composition. According to the present invention, an increase in liquefaction of mucus or sputum can be any measurable or detectable increase in the level of liquefaction of mucus or sputum as compared to a prior level of liquefaction, and is preferably a statistically significant increase (i.e., differences in measured level of liquefaction between the patient sample and a baseline control are statistically significant with a degree of confidence of at least $p<0.05$). Typically, the "baseline control" is a patient sample prior to the administration of the treatment, since normal, healthy individuals generally cannot produce a quantity of sputum sufficient to serve as a control, although sputum from a normal, healthy individual is not excluded as a baseline control. Additionally, a decrease is viscosity results in an improvement of lung function. This improvement can be determined by various means including patient reported outcomes, mean time of exacerbation to hospital admission and/or an increase in forced expiratory volume (FEV). In one aspect of the invention, an increase in FEV is described as an increase of at least about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, and 9.5% and about 10% as compared to a sample from the patient prior to contact with a composition or protein of the present invention. Preferably, contact of a protein or composition of the present invention with the mucus or sputum of a patient sample results in an increase of about 2.5% as compared to a sample from the patient prior to contact with a composition or protein of the present invention. Liquefaction of mucus or sputum and/or decrease in viscosity can be measured using any suitable technique known in the art, including, but not limited to, compaction assays as described in the Examples section. In such an assay, the amount of mucus or sputum in a solid phase (gel) versus aqueous phase (liquid) is measured. In other aspects of the invention, the relative viscosity or cohesiveness of mucus or sputum can be measured using other parameters or indicators including, but not limited to, viscoelasticity (measured, for example, by magnetic microrheometry), glycoprotein content, or DNA content. In another aspect of the invention the change in mucus protein disulfide bonding can be estimated by the use of reagents such as NEM (N-Ethylmaleimide) that preferentially react with unbound (free) Cys residue thiol groups that are created by the disruption of disulfide bonds (Rancourt, R. et al., *Free Radic Biol Med*, 42(9):1441-1453, 2007). In one aspect of the invention, the level of liquefaction is described as the amount of a given mucus or sputum sample that is in an aqueous (liquid) phase as a percentage of the total volume of the mucus or sputum sample. In a patient with cystic fibrosis, for example, the level of liquefaction of mucus or sputum can be as low as less than 10% or even less than 5% of the total volume. Preferably, contact of a protein or composition of the invention with the mucus or sputum results in a change in the liquefaction of the mucus or sputum of at least about such that at least about 15% of the total volume is in liquid phase, and more preferably, at least about 20% of the total volume is in liquid phase, and more preferably, at least about 25% of the total volume is in liquid phase, and more preferably, at least about 30% of the total volume is in liquid phase, and more preferably, at least about 35% of the total volume is in liquid phase, and more preferably, at least about 40% of the total volume is in liquid phase, and more preferably, at least about 45% of the total volume is in liquid phase, and more preferably, at least about 50% of the total volume is in liquid phase or until the blockage or inhibition of function caused by the mucus has cleared (e.g., until the patient airways are cleared sufficiently to begin expectorating the fluid). In general, it is preferred that the liquefaction of the sputum or mucus in increased in small, gradual increments until the airway or other blocked passage (e.g., in the gastrointestinal or reproductive tract) is cleared, but without excessively liquefying the sputum. Excessive liquefaction of the mucus or sputum is not desired, as it can be detrimental to the patient (e.g., liquefied sputum could flow backward and flood the small airways with a thin liquid, that may also be infected, before the sputum can be cleared by the patient). Preferably, the contact of a protein, peptide or composition of the invention with mucus or sputum produces at least about a 1% increase in the liquefaction of the mucus or sputum by volume as compared to prior to the treatment, more preferably, at least about a 2% increase, and so on, in increments of 1%, until the patient airways or other clogged passages are cleared. Once such clearing is attained, e.g. by removal of so-called "mucus plugs" to improve access of drug to the small airways and alveoli, then a lower-dose maintenance therapy may be undertaken in order to keep newly-secreted mucin proteins at a normal state of disulfide bonding.

In one aspect, the therapy is conducted in conjunction with methods to clear the thinned material from the affected tissue (respiratory tract, digestive tract, reproductive tract) of the patient. For example, in the case of the respiratory system, one can use the method of the present invention in conjunction with postural drainage, huff coughing and other respiratory exercises, or any other suitable method for expectorating the liquefied mucus or sputum.

According to the present invention, the mucus or sputum in the patient to be treated is contacted with a protein (or composition comprising the protein) that contains a thioredoxin monocysteinic active site in a reduced state. The protein is effective to reduce the viscosity and cohesiveness of sputum or mucus and/or to increase the liquefaction of sputum or mucus as compared to prior to the step of contacting. As described previously, thioredoxin is a protein disulfide reductase found in most organisms that participates in many thiol-dependent cellular reductive processes. In humans, thioredoxin is also referred to as adult T cell leukemia-derived factor (ADF). Intracellularly, most of this ubiquitous low molecular weight (11,700) protein remains reduced. Reduced or oxidized thioredoxin may be able to enter intact cells or absorb to the cell membrane, where a small amount is gradually internalized over time. Native thioredoxin has two vicinal cysteine residues at the active site that in the oxidized protein form a disulfide bridge located in a protrusion from the protein's three-dimensional structure. The flavoprotein thioredoxin reductase catalyzes the NADPH-dependent reduction of this disulfide. In addition, engineered versions of thioredoxin reductase modified for altered cofactor specificity may utilize NADH instead or in addition to NADPH as described in U.S. Pat. No. 7,071,307, hereby incorporated by reference. Small increases in thioredoxin can cause profound changes in sulfhydryl-disulfide redox status in proteins.

In addition to its ability to effect the reduction of cellular proteins, it is recognized that thioredoxin can act directly as an antioxidant (e.g. by preventing oxidation of an oxidizable substrate by scavenging reactive oxygen species) although, unlike other thiols, thioredoxin does not generally contribute to the oxidative stress in a cell by autooxidizing (e.g. generating superoxide radicals through autooxidation). U.S. Pat. No. 5,985,261 to White et al., supra, showed that thioredoxin directly induces the production of MnSOD and that such induction is effected by thioredoxin in a reduced state.

A "thioredoxin monocysteinic active site" of the present invention comprises the amino acid sequence C-X-X-X (SEQ ID NO:17) (native or wild-type sequence comprises the amino acid sequence C-X-X-C having SEQ ID NO:16). As used herein, amino acid residues denoted "C" are cysteine residues and amino acid residues denoted "X" can be any amino acid residue other than a cysteine residue, and in particular, any of the remaining standard 20 amino acid residues. Such a thioredoxin monocysteinic active site of the present invention preferably comprises the amino acid sequence C-G-P-X (SEQ ID NO:18), wherein the native or wild-type sequence comprises the amino acid sequence C-G-P-C (SEQ ID NO:1). A thioredoxin monocysteinic active site can further comprise the amino acid sequence X-C-X-X-X-X (SEQ ID NO:19), wherein the native or wild-type sequence comprises the amino acid sequence X-C-X-X-C-X (SEQ ID NO:20). Preferably, a thioredoxin monocysteinic active site of the present invention comprises the amino acid sequence X-C-G-P-X-X (SEQ ID NO:21), wherein such amino acid residue denoted "G" is a glycine residue, and wherein such amino acid residue denoted "P" is a proline residue, wherein the native or wild-type sequence comprises the amino acid sequence X-C-G-P-C-X (SEQ ID NO:22). More preferably, a thioredoxin monocysteinic active site of the present invention comprises the amino acid sequence W-C-G-P-X-K (SEQ ID NO:23), wherein such amino acid residue denoted "W" is a tryptophan residue, and wherein such amino acid residue denoted "K" is a lysine residue and wherein the native sequence comprises the amino acid sequence W-C-G-P-C-K (SEQ ID NO:3). Preferably, a thioredoxin monocysteinic active site can comprise the amino acid sequence C-X-X-S (SEQ ID NO:24). Such a thioredoxin monocysteinic active site of the present invention preferably comprises the amino acid sequence C-G-P-S (SEQ ID NO:1). A thioredoxin monocysteinic active site can further comprise the amino acid sequence X-C-X-X-S-X (SEQ ID NO:25), X-C-G-P-S-X (SEQ ID NO: 26) or W-C-G-P-S-K (SEQ ID NO:27), wherein amino acid residues denoted "X" can be any amino acid residue other than a cysteine residue. Reference to "thioredoxin active site" includes thioredoxin monocysteinic active sites and native or wildtype thioredoxin active sites.

In one aspect of the invention, the protein containing a thioredoxin monocysteinic active site is a full-length thioredoxin protein or any fragment thereof containing a thioredoxin monocysteinic active site as described structurally and functionally above. Preferred thioredoxin proteins having monocysteinic active sites include prokaryotic thioredoxin, yeast thioredoxin, plant thioredoxin, and mammalian thioredoxin, with human thioredoxin being particularly preferred. The nucleic acid and amino acid sequences of thioredoxins from a variety of organisms are well known in the art and are intended to be encompassed by the present invention. For example, SEQ ID NOs:4-15 represent the amino acid sequences for thioredoxin from *Pseudomonas syringae* (SEQ ID NO:4), *Porphyromonas gingivalis* (SEQ ID NO:5), *Listeria monocytogenes* (SEQ ID NO:6), *Saccharomyces cerevisiae* (SEQ ID NO:7), *Gallus gallus* (SEQ ID NO:8), *Mus musculus* (SEQ ID NO:9), *Rattus norvegicus* (SEQ ID NO:10), *Bos taurus* (SEQ ID NO:11), *Homo sapiens* (SEQ ID NO:12), *Arabidopsis thaliana* (SEQ ID NO:13), *Zea mays* (SEQ ID NO:14), and *Oryza sativa* (SEQ ID NO:15). Referring to each of these sequences, the X-C-G-P-C-X (SEQ ID NO:22) motif (which includes the CGPC motif of SEQ ID NO:1) can be found as follows: SEQ ID NO:4 (positions 33-38), SEQ ID NO:5 (positions 28-33), SEQ ID NO:6 (positions 27-32), SEQ ID NO:7 (positions 29-34), SEQ ID NO:8 (positions 31-36), SEQ ID NO:9 (positions 31-36), SEQ ID NO:10 (positions 31-36), SEQ ID NO:11 (positions 31-36), SEQ ID NO:12 (positions 31-36), SEQ ID NO:13 (positions 59-64), SEQ ID NO:14 (positions 88-93) and SEQ ID NO:15 (positions 94-99). Moreover, the three-dimensional structure of several thioredoxin proteins has been resolved, including human and bacterial thioredoxins. Therefore, the structure and active site of thioredoxins from multiple organisms is well known in the art and one of skill in the art would be able to readily identify and produce fragments or homologues of full-length thioredoxins, including thioredoxins having monocysteinic active sites that can be used in the present invention.

The phrase "in a reduced state" specifically describes the state of the cysteine residues in the active site of a protein or peptide of the present invention. In a reduced state, adjacent cysteine residues form a dithiol (i.e. two free sulfhydryl groups, —SH). In contrast, in oxidized form, such cysteine residues form an intramolecular disulfide bridge; such a molecule can be referred to as cystine. In a reduced state, a monocysteinic thioredoxin active site is capable of participating in redox reactions through the reversible oxidation of its active site thiol to a disulfide, and catalyzes thiol-disulfide exchange reactions that result in covalent linkage to one of the target disulfide Cys. For proteins or peptides of the present invention containing a thioredoxin monocysteinic active site, the N-terminal cysteine in the active site is in a reduced state as a monothiol and is therefore able to form a stable mixed-disulfide with a cysteine on the target protein.

As used herein, a protein of the present invention containing a thioredoxin monocysteinic active site can be a thioredoxin monocysteinic active site per se or a thioredoxin monocysteinic active site joined to other amino acids by glycosidic linkages. Thus, the minimal size of a protein or peptide of the present invention is from about 4 to about 6 amino acids in length, with preferred sizes depending on whether a full-length, fusion, multivalent, or merely functional portions of such a protein is desired. Preferably, the length of a protein or peptide of the present invention extends from about 4 to about 100 amino acid residues or more, with peptides of any interim length, in whole integers (i.e., 4, 5, 6, 7 . . . 99, 100, 101 . . . ), being specifically envisioned. It may also be a short thioredoxin mimetic peptide blocked at the N and C termini as described by Bachnoff et al., *Free Radical Biol Med* 50:1355-67, 2011. In a further preferred embodiment, a protein of the present invention can be a full-length protein or any homologue of such a protein. As used herein, the term "homologue" is used to refer to a protein or peptide which differs from a naturally occurring protein or peptide (i.e., the "prototype" or "wildtype" protein) by modifications to the naturally-occurring protein or peptide, but which maintains the basic protein and side chain structure of the naturally-occurring form, and/or which maintains a basic three-dimensional structure of at least a biologically active portion (e.g., the thioredoxin active site) of the native protein. Such changes include, but are not limited to: changes in one or a few amino acid side chains; changes in one or a few amino acids, including deletions (e.g., a truncated version of the protein or peptide (fragment)), insertions and/or substitutions; changes in stereochemistry of one or a few atoms; and/or minor derivatizations, including but not limited to: methylation, glycosylation, phosphorylation, acetylation, myristoylation, prenylation, palmitoylation, amidation and/or addition of glycosylphosphatidyl inositol. According to the present invention, any protein or peptide useful in the present invention, including homologues of natural thioredoxin proteins, have a thioredoxin monocysteinic active site such that, in a reduced state, the protein or peptide is capable of participating in redox reactions through the oxidation of its active site thiol to a disulfide and/or of decreasing the viscosity or cohesiveness of mucus or sputum or increasing the liquefaction of mucus or sputum. As used herein, a protein or peptide containing a thioredoxin monocysteinic active site can have characteristics similar to thioredoxin, and preferably, is a thioredoxin selected from the group of prokaryotic thioredoxin, fungal thioredoxin (including yeast), plant thioredoxin, or mammalian thioredoxin. In a particularly preferred embodiment, the protein is human thioredoxin.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in homologues, as compared to the wild-type protein, either agonize, antagonize, or do not substantially change, the basic biological activity of the homologue as compared to the naturally occurring protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally-occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

In one embodiment, proteins or peptides containing a thioredoxin monocysteinic active site can be products of drug design or selection and can be produced using various methods known in the art. Such proteins or peptides can be referred to as mimetics. A mimetic refers to any peptide or non-peptide compound that is able to mimic the biological action of a naturally-occurring peptide, often because the mimetic has a basic structure that mimics the basic structure of the naturally-occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety. Thioredoxin mimetic peptides capable of potent and selective redox activity are described by Bachnoff et al., *Free Radical Biol Med* 50:1355-67 (2011) and incorporated herein by reference in its entirety.

A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Diversity-creation methods such as the foregoing can be combined with other techniques designed to improve function or pharmacology, especially for reduced-size molecules like active-site mimetics. For example, one approach that has shown promise in early-stage studies is hydrocarbon-stapled α-helical peptides, a novel class of synthetic miniproteins locked into their bioactive α-helical fold through the site-specific introduction of a chemical brace, an all-hydrocarbon staple. Stapling can greatly improve the pharmacologic performance of peptides, increasing their target affinity and proteolytic resistance, while creating smaller peptide versions of larger proteins/enzymes that are suitable for chemical synthesis (Verdine, G. L. and Hilinsky, G. J., *Methods Enzymol*, 503:3-33, 2012).

In one embodiment of the present invention, a protein suitable for use in the present invention has an amino acid sequence that comprises, consists essentially of, or consists of a full length sequence of a thioredoxin protein or any fragment thereof that has a thioredoxin monocysteinic active site as described herein. For example, any one of the native sequences of SEQ ID NOs 4-15 or a fragment or other homologue thereof that contains a thioredoxin monocysteinic active site as described herein is encompassed by the invention. Such homologues can include proteins having an amino acid sequence that is at least about 10% identical to the amino acid sequence of a full-length thioredoxin protein, or at least 20% identical, or at least 30% identical, or at least 40% identical, or at least 50% identical, or at least 60% identical, or at least 70% identical, or at least 80% identical, or at least 90% identical, or greater than 95% identical to the amino acid sequence of a full-length thioredoxin protein, including any percentage between 10% and 100%, in whole integers (10%, 11%, 12%, . . . 98%, 99%, 100%).

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
  Reward for match=1
  Penalty for mismatch=−2
  Open gap (5) and extension gap (2) penalties
  gap x_dropoff (50) expect (10) word size (11) filter (on)
For blastp, using 0 BLOSUM62 matrix:
  Open gap (11) and extension gap (1) penalties
  gap x_dropoff (50) expect (10) word size (3) filter (on).

A protein useful in the present invention can also include proteins having an amino acid sequence comprising at least 10 contiguous amino acid residues of any full-length thioredoxin protein containing a monocysteinic active site (native sequences represented by SEQ ID NOs:4-15, i.e., 10 contiguous amino acid residues having 100% identity with 10 contiguous amino acids of a reference sequence). In other embodiments, a homologue of a thioredoxin protein includes amino acid sequences comprising at least 15, or at least 20, or at least 25, or at least 30, or at least 35, or at least 40, or at least 45, or at least 50, or at least 55, or at least 60, or at least 65, or at least 70, or at least 75, or at least 80 contiguous amino acid residues of the amino acid sequence of a naturally occurring thioredoxin protein, and so on, up to the full-length of the protein, including any intervening length in whole integers (10, 11, 12, . . . ) and which comprises a monocysteinic active site.

According to the present invention, the term "contiguous" or "consecutive", with regard to sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a protein useful in the present invention includes a protein having an amino acid sequence that is sufficiently similar to a natural thioredoxin amino acid sequence that a nucleic acid sequence encoding the homologue is capable of hybridizing under moderate, high or very high stringency conditions (described below) to (i.e., with) a nucleic acid molecule encoding the natural thioredoxin protein (i.e., to the complement of the nucleic acid strand encoding the natural thioredoxin amino acid sequence). Such hybridization conditions are described in detail below.

A nucleic acid sequence complement of nucleic acid sequence encoding a thioredoxin protein of the present invention refers to the nucleic acid sequence of the nucleic acid strand that is complementary to the strand that encodes thioredoxin. It will be appreciated that a double-stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes an amino acid sequence of a thioredoxin protein, and/or with the complement of the nucleic acid sequence that encodes such amino acid sequence. Methods to deduce a complementary sequence are known to those skilled in the art.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

A protein of the present invention can also be a fusion protein that includes a segment containing a thioredoxin monocysteinic active site and a fusion segment that can have a variety of functions. For example, such a fusion segment can function as a tool to simplify purification of a protein of the present invention, such as to enable purification of the resultant fusion protein using affinity chromatography. A suitable fusion segment can be a domain of any size that has the desired function (e.g., imparts increased stability to a protein, imparts increased immunogenicity to a protein, and/or simplifies purification of a protein). It is within the scope of the present invention to use one or more fusion segments. Fusion segments can be joined to amino and/or carboxyl termini of the segment containing a thioredoxin monocysteinic active site. Linkages between fusion segments and thioredoxin active site-containing domains of fusion proteins can be susceptible to cleavage in order to enable straightforward recovery of the thioredoxin monocysteinic active site-containing domains of such proteins. Fusion proteins are preferably produced by culturing a recombinant cell transformed with a fusion nucleic acid molecule that encodes a protein including the fusion segment attached to either the carboxyl and/or amino terminal end of a thioredoxin monocysteinic active site-containing domain.

In one embodiment, a protein or peptide containing a thioredoxin monocysteinic active site suitable for use with the method of the present invention comprises a protein or peptide containing a thioredoxin monocysteinic active site derived from a substantially similar species of animal as that to which the protein is to be administered. In another embodiment, any protein or peptide containing a thioredoxin monocysteinic active site, including from diverse sources such as microbial, plant and fungus can be used in a given patient.

In one embodiment of the present invention, any of the amino acid sequences described herein, such as the amino acid sequence of a naturally occurring thioredoxin protein or thioredoxin containing a monocysteinic active site, can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally-occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

In another embodiment, a protein or peptide containing a thioredoxin monocysteinic active site suitable for use with the method of the present invention comprises an isolated, or biologically pure, protein. As such, "isolated" and "biologically pure" do not necessarily reflect the extent to which the protein has been purified. An isolated protein of the present invention can, for example, be obtained from its natural source, be produced using recombinant DNA technology (e.g., polymerase chain reaction (PCR) amplification, cloning), or be synthesized chemically.

In yet another embodiment, a chemically-synthetic protein or peptide containing a thioredoxin monocysteinic active site of the present invention may also refer to a stabilized version, such as one containing an active site constrained structurally by stapled peptide technology, by cyclization, or by constraint at the N or C termini.

Preferably, the protein containing a thioredoxin monocysteinic active site to be used in methods of the invention have a half-life in vivo that is sufficient to cause a measurable or detectable increase in liquefaction (or decrease in the viscosity or cohesiveness) of mucus or sputum in a patient, and or to cause a measurable, detectable or perceived therapeutic benefit to the patient that is associated with the mucus and sputum in the patient. Such half-life can be effected by the method of delivery of such a protein. A protein of the present invention preferably has a half-life of greater than about 5 minutes in an animal, and more preferably greater than about 4 hours in an animal, and even more preferably greater than about 16 hours in an animal. In a preferred embodiment, a protein of the present invention has a half-life of between about 5 minutes and about 24 hours in an animal, and preferably between about 2 hours and about 16 hours in an animal, and more preferably between about 4 hours and about 12 hours in an animal.

Further embodiments of the present invention include nucleic acid molecules that encode a protein or peptide containing a thioredoxin monocysteinic active site. Such nucleic acid molecules can be used to produce a protein that is useful in the method of the present invention in vitro or in vivo. A nucleic acid molecule of the present invention includes a nucleic acid molecule comprising, consisting essentially of, or consisting of, a nucleic acid sequence encoding any of the proteins described previously herein. In accordance with the present invention, an isolated nucleic acid molecule is a nucleic acid molecule (polynucleotide) that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. An isolated nucleic acid molecule of the present invention can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode the desired protein of the present invention or to form stable hybrids under stringent conditions with natural gene isolates. An isolated nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a given protein useful in the present invention can vary due to degeneracies.

According to the present invention, reference to a gene includes all nucleic acid sequences related to a natural (i.e. wildtype) gene as well as those related to the thioredoxin monocysteinic active site, such as regulatory regions that control production of the protein encoded by that gene (such as, but not limited to, transcription, translation or post-translation control regions) as well as the coding region itself. In another embodiment, a gene can be a naturally occurring allelic variant that includes a similar but not identical sequence to the nucleic acid sequence encoding a given protein. Allelic variants have been previously described above. The phrases "nucleic acid molecule" and "gene" can be used interchangeably when the nucleic acid molecule comprises a gene as described above.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on protein biological activity. Allelic variants and protein homologues (e.g., proteins encoded by nucleic acid homologues) have been discussed in detail above.

A nucleic acid molecule homologue can be produced using a number of methods known to those skilled in the art (e.g., as described in Sambrook et al., ibid). For example, nucleic acid molecules can be modified using a variety of techniques including, but not limited to, by classical mutagenesis and recombinant DNA techniques (including without limitation site-directed mutagenesis, chemical treatment, restriction enzyme cleavage, ligation of nucleic acid fragments and/or PCR amplification), or synthesis of oligonucleotide mixtures and chemical ligation, or in vitro or in vivo recombination, of mixtures of molecular groups to "build" a re-assorted library of nucleic acid molecules comprising a multiplicity of combinations thereof by the process of gene shuffling (i.e., molecular breeding; see, for example, U.S. Pat. No. 5,605,793 to Stemmer; Minshull and Stemmer, *Curr. Opin. Chem. Biol.* 3:284-290, 1999; Stemmer, *P.N.A.S. USA* 91:10747-10751, 1994, all of which are incorporated herein by reference in their entirety). These and other similar techniques known to those skilled in the art can be used to efficiently introduce multiple simultaneous changes in the protein. Nucleic acid molecule homologues can subsequently be selected by hybridization with a given gene, or be screened by expression directly for function and biological activity of proteins encoded by such nucleic acid molecules.

One embodiment of the present invention relates to a recombinant nucleic acid molecule that comprises the isolated nucleic acid molecule described above which is operatively linked to at least one transcription control sequence. More particularly, according to the present invention, a recombinant nucleic acid molecule typically comprises a recombinant vector and the isolated nucleic acid molecule as described herein. According to the present invention, a recombinant vector is an engineered (i.e., artificially produced) nucleic acid molecule that is used as a tool for manipulating a nucleic acid sequence of choice and/or for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is, nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid sequences of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a replicating plasmid) or it can be integrated into the chromosome of a recombinant host cell, although it is preferred if the vector remain separate from the genome for most applications of the invention. The entire vector can remain in place within a host cell, or under certain conditions, the plasmid DNA can be deleted, leaving behind the nucleic acid molecule of the present invention. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., the protein containing a thioredoxin monocysteinic active site) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector that enable the transcription and translation of the nucleic acid sequence within the recombinant host cell.

In another embodiment of the invention, the recombinant nucleic acid molecule comprises a viral vector. A viral vector includes an isolated nucleic acid molecule of the present invention integrated into a viral genome or portion thereof, in which the nucleic acid molecule is packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

Typically, a recombinant nucleic acid molecule includes at least one nucleic acid molecule of the present invention operatively linked to one or more expression control sequences. As used herein, the phrase "recombinant molecule" or "recombinant nucleic acid molecule" refers primarily to a nucleic acid molecule or nucleic acid sequence operatively linked to an expression control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence in a manner such that the molecule is able to be expressed when transfected (i.e., transformed, transduced, transfected, conjugated or conduced) into a host cell. Transcription control sequences are expression control sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell or organism into which the recombinant nucleic acid molecule is to be introduced. Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those that are integrated into the host cell chromosome, also contains secretory signals (i.e., signal-segment or signal-sequence nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Other signal sequences include those capable of directing periplasmic or extracellular secretion, or retention within desired compartments. Suitable leader sequences include a leader sequence that is naturally associated with the protein, or any heterologous leader sequence capable of directing the delivery and insertion of the protein to the membrane of a cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells or plants. In microbial systems, the term "transformation" is used to describe an inherited change due to the acquisition of exogenous nucleic acids by the microorganism and is essentially synonymous with the term "transfection." However, in animal cells, transformation has acquired a second meaning which can refer to changes in the growth properties of cells in culture (described above) after they become cancerous, for example. Therefore, to avoid confusion, the term "transfection" is preferably used with regard to the introduction of exogenous nucleic acids into animal cells, and is used herein to generally encompass transfection of animal cells and transformation of plant cells and microbial cells, to the extent that the terms pertain to the introduction of exogenous nucleic acids into a cell. Therefore, transfection techniques include, but are not limited to, transformation, particle bombardment, electroporation, microinjection, lipofection, adsorption, infection and protoplast fusion.

In one embodiment, a composition comprising a protein or peptide containing a thioredoxin monocysteinic active site in a reduced state is used for decreasing the viscosity of excessively viscous mucus or sputum. The composition comprises the protein containing a thioredoxin monocysteinic active site, and may include one or more additional agents or compounds, such as other agents or compounds that can be used to reduce/decrease excessively viscous or cohesive mucus or sputum or increase the liquefaction of such mucus or sputum. Examples of such as other agents or compounds are known in the art and include, but are not limited to, purified rhDNase, N-acetylcysteine, nacystelyn (an N-acetyl-L-cysteine derivative), GSH, and gelsolin. In addition, mucoactive agents like mannitol or hypertonic saline may be used in combination with monocysteinic active site thioredoxin.

In one embodiment, a composition, including a pharmaceutical composition can be used to deliver a nucleic acid molecule encoding a protein or peptide containing a thioredoxin monocysteinic active site to a cell in the patient to be treated (e.g., an epithelial cell in the lung or airways), such that the cell can become transfected with and express the protein, and so that the protein can contact mucus or sputum in the microenvironment of the cell.

A composition, including a pharmaceutical composition, can also include, for example, a pharmaceutically acceptable carrier, which includes pharmaceutically acceptable excipients and/or delivery vehicles, for delivering a protein or nucleic acid molecule or other regulatory compound to a patient. Additionally, a composition, including a pharmaceutical composition of the present invention can be administered to a patient in a pharmaceutically acceptable carrier. As used herein, a pharmaceutically acceptable carrier refers to any substance suitable for delivering a therapeutic protein, nucleic acid or other compound useful in the method of the present invention to a suitable in vivo or ex vivo site. Preferred pharmaceutically acceptable carriers are capable of maintaining a protein, nucleic acid molecule or compound in a form that, upon arrival of the protein, nucleic acid molecule or compound at the desired site (e.g., the site where the mucus or sputum to be treated is secreted or drains), is capable of contacting the mucus or sputum (in the case of a protein or compound) or of entering the cell and being expressed by the cell and secreted (in the case of a nucleic acid molecule) so that the expressed protein in a reduced state can contact the mucus or sputum. Suitable excipients of the present invention include excipients or formularies that transport or help transport, but do not specifically target a therapeutic agent (protein, nucleic acid or compound) to a cell, tissue or fluid (mucus or sputum) (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Preparations for inhalation of therapeutic agents may also include surfactant molecules.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

One type of pharmaceutically acceptable carrier includes a controlled-release formulation that is capable of slowly releasing a composition of the present invention into a patient. As used herein, a controlled-release formulation comprises one or more therapeutic agents of the present invention in a controlled-release vehicle. Suitable controlled-release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Such controlled-release vehicles may also incorporate reducing agents to maintain a thioredoxin monocysteinic active site in a reduced state during storage and delivery. Suitable delivery vehicles for nucleic acids include, but are not limited to liposomes, viral vectors or other delivery vehicles, including ribozymes.

A suitable, or effective, amount of a protein or peptide containing a thioredoxin monocysteinic active site to administer to a patient is an amount that is capable of: participating in redox reactions through the reversible oxidation of its active site thiol to a disulfide, catalyzing thiol-disulfide exchange reactions, and particularly, decreasing the viscosity or cohesiveness of mucus or sputum and/or increasing the liquefaction of mucus or sputum in a patient, sufficient to provide a therapeutic benefit to the patient. Decreases in the viscosity or cohesiveness or increases in the liquefaction of mucus or sputum can be measured, detected or determined as described previously herein or by any suitable method known to those of skill in the art. As discussed above, such measurements include determining and comparing the percentage of free thiols in a sample of mucus or sputum from the patient prior to after contact with a suitable or effective amount of a protein or peptide containing a thioredoxin monocysteinic active site, as well as determining and comparing the FEV level of the patient prior to after contact with a suitable or effective amount of a protein or peptide containing a thioredoxin monocysteinic active site in a reduced state.

In one embodiment, a suitable, or effective, amount of a protein or peptide containing a thioredoxin monocysteinic active site to be administered to a patient comprises between about 10 µmoles/kg, 15 µmoles/kg, 20 µmoles/kg, 25 µmoles/kg, 30 µmoles/kg, 35 µmoles/kg, 40 µmoles/kg, 45 µmoles/kg, 50 µmoles/kg, 55 µmoles/kg, 60 µmoles/kg, 65 µmoles/kg, 70 µmoles/kg, 75 µmoles/kg, 80 µmoles/kg, 85 µmoles/kg, 90 µmoles/kg, 95 µmoles/kg, 100 µmoles/kg, 105 µmoles/kg, 110 µmoles/kg, 115 µmoles/kg, 120 µmoles/kg, 125 µmoles/kg, 130 µmoles/kg, 135 µmoles/kg, 140 µmoles/kg, 145 µmoles/kg, 150 µmoles/kg, 175 µmoles/kg, 200 µmoles/kg, 225 µmoles/kg, 250 µmoles/kg, 275 µmoles/kg, 300 µmoles/kg, 325 µmoles/kg, 350 µmoles/kg, 375 µmoles/kg, 400 µmoles/kg, 425 µmoles/kg, 450 µmoles/kg, 475 µmoles/kg, 500 µmoles/kg, 525 µmoles/kg, 550 µmoles/kg, 575 µmoles/kg, 600 µmoles/kg, 625 µmoles/kg, 650 µmoles/kg, 675 µmoles/kg, 700 µmoles/kg, 725 µmoles/kg, 750 µmoles/kg, 775 µmoles/kg, 800 µmoles/kg, 825 µmoles/kg, 850 µmoles/kg, 875 µmoles/kg, 900 µmoles/kg, 925 µmoles/kg, 950 µmoles/kg, 975 µmoles/kg, 1000 µmoles/kg, 1100 µmoles/kg, 1200 µmoles/kg, 1300 µmoles/kg, 1400 µmoles/kg, 1500 µmoles/kg, 1600 µmoles/kg, 1700 µmoles/kg, 1800 µmoles/kg, 1900 µmoles/kg, 2000 µmoles/kg, 2100 µmoles/kg, 2200 µmoles/kg, 2300 µmoles/kg, 2400 µmoles/kg or about 2500 µmoles/kg body weight of a patient.

In another embodiment, if the route of delivery is aerosol delivery to the lung or a similar route, an amount of a protein or peptide containing a thioredoxin monocysteinic active site to be administered to a patient comprises between about 0.25 mg per dosing unit (e.g., a dosing unit for a human is typically about 2-3 ml) to about 100 mg per dosing unit. Preferably, an amount of a protein or peptide containing a thioredoxin monocysteinic active site to be administered to a patient comprises about 0.25 mg, 0.50 mg, 1.0 mg, 5.0 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or about 100 mg per dosing unit. Depending on the device used for aerosol delivery, some aerosol delivery devices only allow for about 10% of the volume in the aerosol to actually be delivered to the lung. However, when the delivery device is a vibrating mesh nebulizer, about 90% of the volume in the aerosol can be delivered. Electronic vibrating-mesh nebulizers, are capable of delivering drugs far more rapidly and are smaller, more portable devices that are greatly preferred by CF patients (Geller, D. E., *Pediatric Pulmonology*, 43(S9): S5-S17, 2008). Vibrating-mesh nebulizers also are more efficient at delivering drugs with less residual dose vs. air-jet nebulizers. This is particularly significant for reducing treatment costs as smaller doses are required to achieve therapeutic benefit. Devices such as these also do not result in reduced biological activity of proteins (Kesser, K. C., et al. *Resp Care*, 54(6):754-768, 2009; Scherer, T., et al. *J Pharm Sci*, 100(1): 98-109, 2011). Therefore, for other routes of administration when the volume of the composition that will be delivered to the site is greater, it will readily be seen that lower doses of the protein or peptide comprising a thioredoxin active site may be used.

The optimum amount of a protein of the present invention to be administered to an animal will vary depending on the route of administration. For instance, if the protein is administered by an inhaled (aerosol) route, the optimum amount to be administered may be different from the optimum amount to be administered by intratracheal microspray. It is within the ability of one skilled in the art to vary the amount depending on such route of administration. It is important to note that a suitable amount of a protein of the present invention is an amount that has the desired function without being toxic to an animal. Other routes of administration include but are not limited to oral administration, especially for the treatment of digestive mucus, or topical for the treatment of reproductive mucus.

In a one embodiment of the present invention, a composition, including a pharmaceutical composition, of the present invention that contains a protein comprising a thioredoxin monocysteinic reactive site is further formulated with one or more agents that maintains the thioredoxin active site in a reduced state following initial reduction using reducing agents. Such reducing agents used in the present invention include, but are not limited to, dithithreitol (DTT), lipioc acid, NADH or NADPH-dependent thioredoxin reductase, ethylenediaminetetraacetic acid (EDTA), reduced glutathione, dithioglycolic acid, 2-mercaptoehtanol, Tris-(2-carboxyethyl)phoshene, N-acetyl cysteine, NADPH, NADH and other biological or chemical reductants.

As discussed above, a composition, including a pharmaceutical composition, of the present invention is administered to a patient in a manner effective to deliver the composition, and particularly the protein comprising a thioredoxin monocysteinic active site and/or any other compounds in the composition, to a target site (e.g., mucus or sputum to be treated for proteins and compounds, a target host cell that will be or is in the environment of the mucus or sputum to be treated for recombinant nucleic acid molecules). Suitable administration protocols include any in vivo or ex vivo administration protocol.

According to the present invention, an effective administration protocol (i.e., administering a composition of the present invention in an effective manner) comprises suitable dose parameters and modes of administration that result in contact of the protein containing a thioredoxin monocysteinic active site and/or other compound in the composition with the mucus or sputum to be treated, preferably so that the patient obtains some measurable, observable or perceived benefit from such administration. In some situations, by sampling the mucus or sputum from the patient, effective dose parameters can be determined using methods as described herein for assessment of mucus or sputum viscosity or liquefaction. Alternatively, effective dose parameters can be determined by experimentation using in vitro samples, in vivo animal models, and eventually, clinical trials if the patient is human. Effective dose parameters can be determined using methods standard in the art for a particular disease or condition. Such methods include, for example, determination of survival rates, side effects (i.e., toxicity) and progression or regression of disease, as well as relevant physiological parameters such as forced expiratory volume in one second (FEV1).

According to the present invention, suitable methods of administering a composition of the present invention to a patient include any route of in vivo administration that is suitable for delivering the composition to the desired site into a patient. The preferred routes of administration will be apparent to those of skill in the art, depending on whether the compound is a protein or other compound (e.g., a drug), to what part of the body the composition is to be administered, and the disease or condition experienced by the patient. In general, suitable methods of in vivo administration of a monocysteinic active site thioredoxin include, but are not limited to, dermal delivery, intratracheal administration, inhalation (e.g., aerosol), nasal, oral, pulmonary administration, and impregnation of a catheter. Aural delivery can include ear drops, intranasal delivery can include nose drops or intranasal injection, and intraocular delivery can include eye drops or the use of suitable devices for passage of the drug across the sclera. Aerosol (inhalation) delivery can also be performed using methods standard in the art (see, for example, Stribling et al., *Proc. Natl. Acad. Sci. USA* 189: 11277-11281, 1992, which is incorporated herein by reference in its entirety). Oral delivery can include solids and liquids that can be taken through the mouth, for example, as tablets or capsules, as well as being formulated into food and beverage products or animal feed or feed pellets. Other routes of administration that are useful for mucosal tissues include bronchial, intranasal, other inhalatory, rectal, topical, transdermal, vaginal, transcervical, pericervical and urethral routes. In addition, administration protocols can include pretreatment devices, such as application of the protein, peptide or composition in a diaphragm (e.g., to the cervix) for use in applications such as infertility. In a preferred embodiment of the present invention, when the protein or composition of the invention is administered to treat excessively or abnormally viscous or cohesive sputum or mucus in the respiratory tract (airways), a protein or peptide (or composition) containing a thioredoxin monocysteinic active site or other compound is administered by a route including, but not limited to, inhalation (i.e. by inhaling an aerosol, e.g., in or with surfactants); direct installation into the lung via a bronchoscope, endotracheal tube and/or via any artificial ventilation device; nasal administration (intranasal or transnasal), bronchial, or intratracheally (i.e. by injection directly into the trachea or tracheostomy), either directly or via lipid-encapsulation or surfactant. Any conceivable method of introducing the composition or protein into the airways so that it can contact the mucus or sputum therein is encompassed by the invention.

In the methods of the present invention, compositions, including pharmaceutical compositions can be administered to any member of the Vertebrate class, including, without limitation, primates, rodents, livestock, chickens, turkeys and domestic pets. Preferred patients to protect are humans.

Another embodiment of the present invention relates to a composition comprising a protein or peptide containing a thioredoxin monocysteinic active site, wherein the cysteine in the monocysteinic active site is covalently bound to a cysteine residue in a mucus protein. Mucus proteins include but are not limited to respiratory mucus proteins and digestive tract mucus proteins. Mucus proteins include mucins, such as the heavily disulfide-bonded mucins MUC5AC and MUC5B. For example, following an initial catalytic reaction at the N-terminal thioredoxin active site cysteine in a thiol-exchange reaction with a disulfide bond of a mucus protein, the protein or peptide containing a thioredoxin monocysteinic acid can be bound covalently via the N-terminal cysteine to a mucus protein and thus be refractory to repeated reduction and catalysis. Covalent linkage of a thioredoxin containing the monocysteinic active site to its mucin target prevents cellular uptake and internalization of thioredoxin by sequestration on the mucus, which has the dual benefits of preventing epithelial uptake and off-target effects due to undesired thioredoxin activity within cells, while at the same time facilitating clearance of mucus-linked spent drug from the body.

A further embodiment of the present invention relates to a method to decrease viscosity of mucus or sputum in a patient that has excessively viscous or cohesive mucus or sputum by administering a composition comprising a protein or peptide containing a thioredoxin monocysteinic active site, wherein the protein covalently binds to a cysteine residue in a mucus protein. In one aspect, the mucus protein is a mucin. In yet another aspect, the thioredoxin monocysteinic active site is in a reduced state. In yet another aspect, the mucus protein can be a respiratory mucus protein or a digestive tract mucus protein, or a reproductive tract mucus protein.

Another embodiment of the present invention relates to a method to decrease viscosity of mucus or sputum in a patient that has excessively viscous or cohesive mucus or sputum by contacting the mucus or sputum of the patient with a composition comprising a disulfide bond reducing agent and a cysteine-blocking agent. The disulfide bond reducing agent and a cysteine-blocking agent can be the same molecule, including but not limited to a protein or peptide containing a thioredoxin monocysteinic active site, or they can be different molecules. The disulfide bond reducing agent can be dithithreitol (DTT), ethylenediaminetetraacetic acid (EDTA), GSH, dithioglycolic acid, 2-mercaptoethanol, N-acetyl cysteine, Tris-(2-carboxyethyl)phosphine, or other pharmaceutically-compatible reducing agents known to the art. The cysteine-blocking agent can be iodoacetamide, iodoacetic acid, or other alkylation agents, or a cysteine-specific antibody or other affinity-encoding protein or peptide composition or antibody mimetic. The cysteine-blocking agent binds to a cysteine that was in a disulfide bond in the mucus protein prior to the bond being reduced. The cysteine-blocking agent prevents the thiol group of the cysteine in the mucus from reforming a disulfide bond.

Yet another embodiment of the present invention relates to a method to treat a patient having excessively viscous or cohesive mucus by administering to the patient a composition comprising at least one compound having a thioredoxin active site that is incapable of cellular uptake. The compound can be a protein or peptide comprising a thioredoxin monocysteinic active site. The compound can also be a fusion protein comprising a thioredoxin portion and a cell surface receptor ligand portion. In this embodiment, the cell surface receptor ligand portion binds to a cell surface receptor thereby preventing cellular uptake of the fusion protein. The compound can be a combination of a protein or peptide comprising a thioredoxin active site and a blocking compound for the cysteine corresponding to the cysteine at position 35 of SEQ ID NO:12. In a preferred embodiment, the blocking compound can be an antibody or antibody mimetic that binds to the thioredoxin molecule and thus blocks the cysteine at position 35 of SEQ ID NO:12. In this regard, the term "blocks" refers to interfering with the ability of the cysteine at position 35 of SEQ ID NO:12 for example to form an intramolecular disulfide bond with the cysteine at position 32 of SEQ ID NO:12.

A further embodiment of the present invention relates to a method of preventing systemic exposure to a drug substance in a patient. The method includes the step of administering the drug to the patient by a delivery route including but not limited to a pulmonary, oral or topical delivery route. The drug can form a covalent bond to its target site once administered. This mechanism of action is distinct from known drug mechanisms of action as many drugs act by molecular interactions wherein ligands bind to receptors with reversible binding of the molecules to the receptors. In a preferred embodiment, the drug substance is a thiol-containing drug wherein the thiol group forms a covalent bond with another thiol group at its target site. For example, the drug can comprise a protein or peptide containing a thioredoxin monocysteinic active site in a reduced state. In yet another preferred embodiment the target site is extracellular and the drug is administered by an extracellular delivery route.

Still another embodiment of the present invention relates to a pharmaceutical composition comprising a protein or peptide containing a thioredoxin monocysteinic active site in a reduced state and further comprising at least one saccharide or saccharide derivative capable of stabilizing the redox-active thiol group. The saccharide or saccharide derivative can be sucrose, sucralose, lactose, trehalose, maltose, galactose, raffinose, mannose or mannitol. By redox-active thiol group it is meant a thiol group that may exist in either a reduced state (—SH) or an oxidized state (—S—S—). The term "stabilizing" includes, for example, reducing the rate of oxidation of the redox-active thiol group in a reduced state when the polypeptide is present in a pharmaceutical composition with the saccharide or saccharide derivative relative to a composition in which the saccharide or saccharide derivative is omitted. By "saccharide" it is meant any mono-, di-, oligo- or poly-saccharide. Examples of saccharides are glucose, fructose, sucrose, lactose, maltose, galactose, raffinose, inulin, dextran trehalose, sucralose, mannose and mannitol. By saccharide derivative it is meant a compound that structurally resembles the saccharide from which it is derived. For example, sucralose, which is a chlorinated sucrose, would be considered a saccharide derivative of sucrose. Further derivatives include, for example, alditol derivatives for example mannitol and xylitol. Preferred compositions of the present invention comprise non-reducing saccharides, for example raffinose, trehalose, stachyose and particularly sucrose.

Another embodiment of the present invention relates to an animal feed composition comprising a protein or peptide containing a thioredoxin monocysteinic active site in a reduced state. Examples of animal feed include but are not limited to hay, straw, silage, compressed and pelleted feeds, oils and mixed rations, sprouted grains, legumes, crop residue, grain, cereal crop, and corn.

The following examples are provided for the purpose of illustration and are not intended to limit the scope of the present invention.

EXAMPLES

Example 1

This example demonstrates the expression and purification wild-type Trx (also referred to herein as "rhTxr") and monocysteinic active site rhTrx (also referred to herein as "r(Cys)hTrx") proteins. Protein expression levels and post-transcriptional expression fidelity of rhTrx and r(Cys)hTrx were maximized by codon optimization of the human Trx-1 DNA sequence as described by Harris et al., *Biotechnol Biogen* 109:1987-97 (2012), herein incorporated by reference in its entirety. Cloning of synthetic constructs into suitable vectors for production in *E. coli* was performed allowing both wild-type and monocysteinic active site r(Cys)hTrx mutant proteins to be produced at the µg scales. Several expression tag and purification strategies were evaluated at laboratory scale, as well as affinity cleavage to facilitate purification away from endotoxin and endogenous host thioredoxins.

Preparation of rhTrx and r(Cys)hTrx in *E. coli*

The rhTrx gene encoding the 105 amino acid mature rhTrx protein including the initiator methionine was optimized for *E. coli* expression and synthesized (DNA2.0, Inc.). The gene was subcloned into the pEV vector, which contained an inducible T7 promoter, kanamycin resistance marker, a 6-histidine tag for Ni-affinity purification and a tobacco etch virus protease cleavage site (TEV). To express the rhTrx, the rhTrx pEV plasmid (verified by sequencing) was transformed into C43 *E. coli* (Lucigen) grown to an optical density of ~0.6 (600 nm) and induced with isopropyl β-D-1-thiogalactopyranoside (IPTG). The protein was extracted from the *E. coli* cells using homogenization and detergent lysis followed by centrifugation. The rhTrx was purified from the *E. coli* lysate using Ni-affinity chromatography. The Ni-affinity purified rhTrx was protease cleaved (TEV) to remove the nickel affinity tag and further purified using ion exchange chromatography and reverse phase high pressure liquid chromatography (HPLC). The purity of the protein was assessed by SDS-PAGE and ion spray mass spectroscopy (LC/MS/MS) and the sequence of the protein was verified by trypsin cleavage of the rhTrx followed by ion trap mass spectroscopy. The protein concentration and endotoxin concentration was determined by the bicinchoninic acid assay (Pierce) and *Limulus* Amoebacyte Assay (Charles River Lab.), respectively. The r(Cys) hTrx protein was prepared following similar methods, but with a r(Cys)hTrx gene optimized and synthesized by DNA2.0. These rhTrx and r(Cys)hTrx proteins were reduced in vitro using DTT which was subsequently removed by dialysis and desalting column treatment.

Example 2

A preferred expression, purification and reduction (activation) strategy for native rhTrx and monocysteinic active site rhTrx (r(Cys)hTrx) proteins utilizing direct expression of mature protein rather than an affinity binding approach is described in this example. r(Cys)hTrx and native Trx control proteins were produced in shake-flask batch cultures and fed-batch fermentations of *E. coli* BL21, and K12-derrived hosts using standard techniques of bacterial fermentation with a range of common constitutive or inducible promoter systems, however sugar-inducible or IPTG-inducible systems were preferred, as these resulted in the highest-expressing strains. Following cell disruption by microfluidizer, supernatants containing soluble Trx were collected by centrifugation and treated with ammonium sulfate (AS) to preferentially precipitate host cell proteins. The resulting Trx-enriched supernatants were filtered using ultrafiltration/diafiltration (UF/DF) for buffer exchange to 15 mM Hepes, 10 mM beta mercaptoethanol (b-ME), 250 mM NaCl. In this buffer, Trx does not bind to a Q-Sepharose HP anion-exchange chromatography (AEC) resin whereas DNA and other impurities bind with high affinity. Following high-salt AEC the Trx-enriched flow-through was exchanged into a low-salt buffer for a second AEC step on a Hi-Trap Q-HP column (GE Healthcare) under reducing conditions (10 mM DTT) followed by buffer exchange to formulation buffer (described below). Alternatively, after AS precipitation the soluble fraction was filtered at 30 kD cutoff and loaded on a hydrophobic interaction chromatography (HIC) column. The eluted material was concentrated and buffer exchanged using a UF/DF cassette of 1 KD and loaded onto a Source Q (anion exchange) column. Thioredoxin proteins were eluted from the ion exchange column using a salt gradient and then an additional UF/DF step to exchange into storage buffer.

Endotoxin was quantified using a *Limulus* Amoebacyte Lysate kit (LAL, Pierce) and any residual endotoxin was removed using a 0.2 micron Mustang E-filter (Pall). Protein identity and yield were determined by SDS-PAGE and Western blot/ELISA at appropriate steps, and total mass and final sequence identity was verified by MALDI and electrospray mass spectrometry. The reducing activity of the Trx formulations were quantified using a DTNB (Ellman's Reagent) reduction assay. Fifty microliters of 2.5 mM rhTrx or r(Cys)hTrx was added to a 96-well plate, followed by 175 microliters of sample buffer and 25 microliters of 6 mM DTNB (5,5'-dithiobis-(2-nitrobenzoic acid). After reactions were initiated by the addition of DTNB, the change in absorbance at 412 nm due to DTNB reduction was measured spectrophotometrically at 30° C. after 15 minutes.

A range of storage buffer conditions, such as those discussed below, are used for compatibility with lyophilization and their ability to stabilize the reduced state of r(Cys)hTrx. The buffer conditions include low pH with reducing sugars, ammonium acetate pH 5.5 with 10 mM b-ME, as well as a buffer formulation previously identified as enhancing storage stability of reduced native Trx (40 mM Na acetate pH 5.5, 0.05% EDTA, 9.25% sucrose). Each buffer condition with Trx is lyophilized and stored for varying times in a dried form, and redox stability of stored protein assessed using DTNB and protein activity assays as described above. For aerosol stability assessment, a PennCentury aerosolizer or nebulizer may be used. Aerosol compounds are collected into 0.1M Tris buffer pH 8.0, 1 mM EDTA containing DTNB at different time points of incubation to determine aerosol stability of the r(Cys)hTrx and native rhTrx. Aggregates are not expected to react with DTNB and hence only the reduced form will be detected. The extinction coefficient of DTNB (14150 at 412 nm) is used to calculate free thiol (SH) groups as a function of recovered protein concentration. Previous studies of intratracheal (IT) delivery of native rhTrx (Rancourt, R. et al., *Free Radic Biol Med,* 42(9):1441-1453, 2007) used normal saline. Addition of redox-stabilizing agents known to be compatible with inhalation delivery, such as methionine, may also be included.

Example 3

This example demonstrates construction and *E. coli* strains for expressing r(Cys)hTrx and native rhTrx. r(Cys)hTrx and native rhTrx control are readily expressible as mature, soluble proteins with various vector systems and laboratory BL21 or K12 strains of *E. coli*. To produce higher-yielding (>1 g/L) Trx-expressing strains of *E. coli*, codon-optimized r(Cys) hTrx and native rhTrx DNA sequences were synthesized and cloned into a range of expression vectors using different intracellular promoters systems including nutrient-depletion based inducible systems, sugar-inducible systems (e.g., rhamnose, xylose, melibiose or other inducible promoters known in the art, e.g. U.S. Pat. No. 7,871,815), or IPTG-inducible systems based on promoters from bacteriophage T3, T5 or T7. Following DNA sequence confirmation expression constructs were transformed into different commonly used BL21/K12 *E. coli* host strains, including strains engineered to lack utilization of molecules used for induction, or which also may have included over-expressed methionine aminopeptidase to improve fidelity of expression at high titers (Liu, M. et al., *Protein Expr Purif* 84(1):130-139, 2012). The resulting production host/vector combinations were grown in medium to high-throughput format deep-well microtiter plates, with shaking at 30-37° C. in minimal medium and screened for expression using methods commonly used in the art, such as gel or capillary electrophoresis. Positive clones were confirmed via SDS-PAGE and Western blot and/or ELISA/ELISPOT. Fed-batch fermentation of the strain was conducted and the yields of protein (r(Cys)hTrx) were assessed by SDS-PAGE and Western blot and/or ELISA/ELISPOT. Proteins were purified and reduced using the methods described in Examples 1 and 2 above, and reduction state of the activated protein was assessed by DTNB assay and specific disulfide bond reduction activity by insulin reduction assay. Sequence identity was analyzed by mass spectrometry (MALDI or electrospray) in order to confirm translational fidelity and proper molecular weight.

Example 4

This example demonstrates the in vitro activity and function of wildtype and monocysteinic active site rhTrx. The activity of rhTrx was assessed by measuring its reducing activity in a standard colorimetric DTNB assay, and by determining its ability to inhibit neutrophil elastase activity. In addition, the ability of r(Cys)hTrx to liquefy human CF mucus as compared to rhTrx was determined, by using a sputum compaction assay, and optionally, by examining the reduction of the viscoelasticity of CF sputum using a specialized rheometer. The rhTrx and r(Cys)hTrx was compared to the standard of care CF mucolytic Pulmozyme (rhDNase I; dornase alfa).

Initial Characterization of rhTrx: Reducing Activity.

The general reducing activity of pre-reduced Trx formulations was quantified using the DTNB reduction assay as previously reported (Rancourt, R. et al., *Free Radic Biol Med*, 42(9):1441-1453, 2007). For enzymatic reduction of rhTrx and r(Cys)hTrx, 50 microliters of assay buffer (100 mM potassium phosphate, pH 7.0, 10 mM EDTA, and 0.05 mg/ml bovine serum albumin) containing 5 or 50 mM rhTrx and 0.5 mM purified TrxR were added to a 96-well plate. Next 175 microliters of sample buffer containing 720 mM NADPH were added, followed by 25 microliters of 6 mM DTNB in sample buffer. To measure the reducing activity of chemically pre-reduced rhTrx, 50 microliters of 2.5 mM rhTrx was added to a 96-well plate, followed by 175 microliters of sample buffer and 25 microliters of 6 mM DTNB. After reactions were initiated by the addition of DTNB, the change in kinetic absorbance at 412 nm due to DTNB reduction was monitored spectrophotometrically at 30 degrees C. Following the same protocol, r(Cys)hTrx was subjected to this assay as well as those described below. The total reducing activity of r(Cys)hTrx was less than rhTrx reflecting the one fewer reduced Cys present in r(Cys)hTrx. However, both proteins were reduced to over 90-95% of their potential reduction state, reflecting full activation.

Inhibition of Neutrophil Elastase (NE) Activity.

An incubation system for determining the effect of rhTrx on NE activity has been described previously (Lee, R., et al. (2005) Am J. Physiol. Lung Cell. Mol. Physiol. 289(5):L875-882). Briefly, Trx was diluted to the desired concentration in phosphate-buffered saline (PBS, pH 7.2). The mixture was added to purified human NE (100 micrograms per ml in PBS, pH 7.2, 0.01% Triton X-100) and incubated at 37 degrees C. for 1 h. The final volume during incubation was 210 microliters, and the concentration of NE was 1.6 micrograms per ml. After incubation, 60 microliter aliquots were tested in triplicate for elastolytic activity. Elastase activity was determined by adding 120 microliters of 0.8 mM N-methoxysuccinyl-Ala-Ala-Pro-Val 4-nitroanilide in PBS (pH 7.2) to the experimental sample and kinetic absorbance was monitored at 405 nm at 37° C. for 4 min. The concentration of elastase used in these experiments was determined to be within the linear range of the assay. The percent NE activity inhibition was determined as: percent inhibition=(1−absorbance change for experimental group/absorbance change for PBS control group). The elastase activity of r(Cys)hTrx was found to be least comparable to rhTrx.

Compaction Assay to Assess Liquefaction of Human CF Sputum.

For all manipulations, CF sputum was handled under a microbiologic hood. rhTrx, r(Cys)hTrx or diluent alone (25 microliters), in relevant concentrations, was added to CF sputum (275 microliters) in a 1.5 ml Eppendorf conical tube and mixed by very brief vortexing. After incubation at 37 degrees C. for 30 min, samples were again briefly mixed and loaded into hematocrit tubes and sealed at both ends. After a 5 minute centrifugation in a hematocrit centrifuge, the percent solids (gel) and percent liquid was determined by direct linear measurement and expressed as percent liquid as follows: 100×liquid/(liquid+solids). For each condition, sputum from at least five different CF patients was measured in triplicate. The liquefaction ability of r(Cys)hTrx was at least comparable to, if not much greater than, rhTrx reflecting the unexpected potency of the r(Cys)hTrx mechanism of action.

Sputum Viscoelasticity Determination.

These measurements are made using a cone-and-plate rheometer as well as qualitatively via direct observation of sputum flow following treatment with thioredoxin. Incubations are conducted using the same sputum handling protocol as described above. Viscoelasticity is assessed using an AR-1000 rheometer (TA Instruments, New Castle, Del.) in oscillation mode with an angular velocity of 1 rad/second at 37° C. For each preparation of Trx, ability to decrease sputum viscoelasticity is assessed in triplicate in sputum obtained from at least 5 different CF patients. The ability to decrease sputum visoelasticity of r(Cys)hTrx is expected to be at least comparable to, if not much greater than, rhTrx reflecting the unexpected potency of the r(Cys)hTrx mechanism of action. Measurement of sputum viscoelasticity by observing the rate of flow of sputum mixed with rhTrx or r(Cys)hTrx in inverted Eppendorf tubes was performed, and in this assay the flow of r(Cys)hTrx was found to be more extensive than rhTrx, DTT and Pulmozyme, and much greater than that of negative (vehicle) controls which exhibited essentially no sputum flow.

Comparison of Efficacy with Standard of Care Mucolytic Agent (rhDNase).

For these studies, relevant concentrations of rhTrx, r(Cys)hTrx and rhDNase were compared by incubation as described above. After 30 minutes, samples were assessed for changes in liquefaction of sputum (compaction assay) and alteration of viscoelasticity. In addition, synergy studies were performed. In these, sputum samples were exposed to rhTrx for 30 min and then rhDNase for 30 min, and, alternatively, rhDNase for 30 min followed by rhTrx for 30 min. These results were compared to the effects of either agent alone. For each condition, sputum from at least five different CF patients were measured in triplicate. Sufficient sputum from individual donors on a given day were required in order to test each of 12 samples (rhTrx ×3, rhDNase ×3, rhTrx+rhDNase ×3, rhDNase+rhTrx ×3) for wildtype and mutant rhTrx variants. In practice, this is, minimally, 4.5-5.0 ml of well-mixed sputum from a single donor/day. The liquefaction ability of r(Cys)hTrx was at least comparable to, if not much greater than, rhDNase. rhDNase, rhTrx, or DTT positive controls.

Human CF Sputum Collection.

Sputum was obtained from adult and pediatric patients with CF as determined by a health care provider. Patients were diagnosed with CF if they demonstrated clinical symptoms and had a sweat chloride value in excess of 60 millimolar in two separate pilocarpine iontophoresis sweat tests and exhibited two allelic CF-producing mutations in subsequent genetic analysis. All samples were donated by either spontaneous expectoration or hypertonic saline induction. Sputum samples containing visibly detectable saliva were discarded. Sputum was kept on ice until delivered to the laboratory, then held at −80 degrees C. until use in O-ring-sealed vials to prevent desiccation.

Example 5

This example demonstrates the enzymatic (FIG. 1*b*) and non-enzymatic (FIG. 1*a*) activity of a protein or peptide containing a thioredoxin monocysteinic active site as compared with a protein or peptide containing a wild-type thioredoxin active site. As illustrated in FIG. 1*a* a non-specific 5,5'-dithiobis-(2-nitrobenzoic acid) (DTNB or Ellman's reagent) reduction reflects the loss of one reducible cysteine in the thioredoxin monocysteinic active site as compared to wildtype. As illustrated in FIG. 1*b* and FIG. 2, a protein or peptide containing a thioredoxin monocysteinic active site surprisingly exhibited greater potency as compared to a protein or peptide containing a wild-type thioredoxin active site in a human sputum compaction assay as well as greater potency on an equimolar basis versus DNase or NAC (FIG. 2). This result is unexpected, given the substantial modification at the active site due to mutation of Cys35, and the observation that the total reducing power was 4/5 that of native thioredoxin by virtue of the loss of one reducible Cys residue in the prior DTNB assay. The surprising increase in potency of the thioredoxin monocysteinic active site was realized to be due to the covalent linkage to mucin protein Cys residues, which had the unanticipated consequence of preventing these Cys from re-forming new disulfide bonds.

Example 6

This example demonstrates the decreased propensity of r(Cys)hTrx (in a reduced, active state) to stimulate release of pro-inflammatory cytokines by cultured primary human bronchial epithelial cells (HBE) as compared to native rhTrx. Donor tissues and cells are provided under the auspices of approved protocols for the protection of the rights of human subjects. HBE cells from normal (i.e. non-diseased) lungs are harvested by enzymatic digestion as previously described (Fulcher, M. L., *Methods Mol Med* 107:183-206, 2005). Disaggregated HBE cells are seeded on 12 mm diameter Transwell Clear supports (Corning) at a density of $2.5 \times 10^5/cm^2$ in a well-defined airway cell media (Fulcher, M. L., 2005 ibid). Cultures are maintained at an air-liquid interface until fully differentiated (about 4-6 weeks) before use.

Thioredoxin Delivery Protocol:

For this study, a device capable of delivering nanoliter volumes of test agent (or control) to the surface of HBE cultures is utilized. This system is designed to be an in vitro model system to mimic the in vivo delivery of an ultrafine mist of nebulized medications to the surface of airway epithelial cells, and represents the ideal way to study the effect of adding therapeutics, such as r(Cys)hTrx. Based on the results of multiple-path particle dosimetry modeling (Anjilvel, S., et al. *Fundam Appl Toxicol* 28(2):41-50, 1995) demonstrating the average deposition rates of Pari LC Star nebulizer over the first 20 generations of airways, the average deposition over the first 6 generations of airways, where the majority of particles are expected to be delivered, is estimated to be ~50 nl/min/cm², over the course of 15 minutes. In these studies, nebulization on a total volume of 750 nl (over 15 minutes) to a total of five different experimental groups is performed. These include: 1) vehicle control (isotonic saline), 2) Native recombinant Trx (500 μm), and 3) three doses of r(Cys)hTrx (10 μm, 250 μm, and 1000 μm). These concentrations represent the "final" airway surface concentration. Following nebulization of the each test reagent (or vehicle control), cultures are returned to the tissue culture incubator and incubated for 24 hours before cytokine analysis.

Cytokine Immunoassay

In this study, the effect of native and r(Cys)hTrx on stimulation of the four major cytokines which are released by HBE cells, including IL-6, IL-8, TNF-α, and IL-1β is assessed. Cytokines in cell-free, un-concentrated culture supernatants are measured using commercially available enzyme-linked immunosorbent assay (ELISA) kits (R&D systems). Samples of basolateral ALI media (Fulcher, M. L., 2005, ibid) are obtained at 24 hours post-nebulization of all five groups, and frozen before analysis. As a background control, clean (un-used) ALI media is subtracted from all values. For each cytokine analysis, positive controls over three decades of concentrations are used to generate appropriate standard curves. Additionally, each "unknown" sample is analyzed in duplicate. Cytokines measured are: TNF-α (lower detection limit of 0.3 pg/ml), IL-6 (lower detection limit of 0.35 pg/ml), IL-8 (lower detection limit of 2.4 pg/ml), and IL-1β (lower detection limit of 1.5 pg/ml). Cross-reactivity of these assays with each other and with other recombinant human cytokines (IL-1a, IL-2, IL-3, IL-4, IL-7, tumor necrosis factor-S, granulocyte colony-stimulating factor, and transforming growth factor-I11) has been previously shown to all below limits of detection.

Sample Size and Statistical Analysis:

Each of the five conditions are evaluated on a total of nine individual HBE cultures. This represents three cultures (n=3) from three different patients (n=3). Such an approach is sufficiently powered statistically to provide an understanding of the inter- and intra-sample variation of each condition. For data analysis, comparison between individual samples/groups is made using two-tailed Student's t-test. For multiple group comparisons, a one-way analysis of variance (ANOVA) is used. Significance for all analyses is set at $p<0.05$.

Proinflammatory Evaluation of r(Cys)hTrx in HBE Cultures from CF Patient Donors.

Human CF primary airway epithelial cell culture: Recent techniques to proliferate and culture human primary airway epithelial cells at an air-liquid interface with mucociliary differentiation, is employed based on methods reported by Schlegel and colleagues (Liu, M. et al., *Protein Expr Purif.* 84(1):130-139, 2012; Suprynowicz, F. A., et al. *Proc. Natl. Acad. Sci. U.S.A.* 109(49):20035-20040, 2012). These methods allow a virtually unlimited supply of primary airway epithelial cells that are still capable of terminal differentiation at ALI, without genetic manipulation. 30 wells are cultured to differentiation at ALI over 30 days from each of three unique CF donors, homozygous for F508del. The cultures are exposed at the apical surface to three concentrations (10 μM, 250 μM and 1000 μM) of rhTrx (wild type) and r(Cys)hTrx followed by collection of both apical and basolateral media samples at 4 and 24 hours after exposure challenge (see Table 1). The media used is serum free, centrifuged to remove debris and stored at −80° C. until use. ELISA assays for human inflammatory cytokines are performed on all samples taken from both the apical and basolateral media. Apical collection occurs by placing 200 μL of sterile PBS on the apical surface and recovering this after 15 min incubation. ELISA for IL-8 and IL-6 are performed for each sample in duplicate (Becker, M. N. et al., *Am J Resp Crit Care Med* 169(5):645-653, 2004). The plan above involving 30 ALI cultures is repeated for each of the three CF donors. Comparison of the results of native rhTrx and r(Cys)hTrx demonstrates that the propensity of thioredoxin to induce proinflammatory cytokine release from differentiated airway epithelial cells of CF patients is attenuated in the monocysteinic Trx vs. native at the concentrations tested.

TABLE 1

| Time after exposure | Diluent Control | rhTrx (500 μM) | r(Cys)hTrx (10 μM) | r(Cys)hTrx (250 μM) | r(Cys)hTrx (1000 μM) |
|---|---|---|---|---|---|
| 4 hr | 3 | 3 | 3 | 3 | 3 |
| 24 hr | 3 | 3 | 3 | 3 | 3 |

Example 7

This example demonstrates the biophysical and biochemical characterization of the effect of r(Cys)hTrx versus native rhTrx on uniform mucus harvested from in vitro HBE cell cultures.

Preparation of Cell Culture Mucus

Human bronchial epithelial cells are grown and maintained as described (Matsui, H., et al., *J Clin Invest* 102(6):1125-1131, 1998). In brief, mucus harvested from cultures is pooled and stored at 4° C. Samples are loaded into dialysis tubes (MWCO=3,500) and concentrated with a polymer absorbent (Spectra/Gel) for 1-5 days at 4° C. The concentrated mucus is then dialyzed against PBS containing 500 µM $MgCl_2$ and 800 µM $CaCl_2$ at 4° C. to establish a proper salt balance (Matsui, H. et al., *Proc Natl Acad Sci USA* 103(48): 18131-18136, 2006).

Macroscopic Rheology:

Concentration and time course assays using a Bohlin Gemini Rheometer in both cone and plate and parallel geometries are performed to assess the bulk, macroscopic biophysical effects of reduced r(Cys)hTrx and native thioredoxin on in vitro HBE mucus properties. Creep recovery experiments are performed in which a known stress (between 0.05 and ~100 Pa) is applied to treated or control mucus for 10 seconds, and the rheological recovery of the fluid is recorded for an additional 50 seconds. In successive runs, the applied stress is increased in a logarithmic fashion until the yield stress of the fluid is reached (i.e. the stress at which the viscosity of the fluid suddenly and dramatically decreases). From the measured parameters the viscosity and elasticity of the fluid is determined as a function of applied stress. Frequency sweeps are performed at both constant stress and strains and used to determine the baseline physical properties of mucus (G' and G" respectively), as well as the viscosity and shear thinning behavior of the fluid. All experiments are performed at 23° C.

High Pressure Liquid Chromatography:

The concentration and molecular mass of mucins in treated and control mucus is assessed by differential refractometry to determine the effect of native thioredoxin and r(Cys)hTrx on mucin structure. Samples (500 µl) are loaded onto a Sepharose S1000 column (Amersham Pharmacia), and eluted with 200 mM sodium chloride/10 mM EDTA at a flow rate 0.5 ml/min. An in-line Dawn EOS laser photometer coupled to a Wyatt/Optilab DSP inferometric refractometer is used to measure light scattering and sample concentration, respectively (Wyatt Technology Corporation). The concentration of the mucins is calculated by integrating the refractive index peak associated with the material eluted in the void volume of the column and employing a value for the refractive-index increment (dn/dc) of 0.165 ml/g, which has been measured previously at 650 nm and found to be reproducible within 5%. The total protein content (mucins and small proteins) of a given mucus sample is determined by similar methods, but with a G-25 column (dn/dc=0.170). The non-mucin (or small protein) content of the sample is determined by subtracting the mass of the mucin content (determined by elution the sample through the S-1000 column) from the total mass of the mucin and protein content (detected by the eluting the sample through the G-25 column). In comparison with gel-based methods, e.g. reducing or non-reducing PAGE, differential refractometry is advantageous in that exact molecular weights and molecular weight distributions are accessible rather than qualitative comparisons. The quantitative advantage of these techniques are particularly important for the study of large glycoproteins such as mucins where no size standards exist and molecular weights often exceed 1 MDa (Gillis, R. B., et al., *Carbohydr Polym* 93(1):178-183, 2013).

Carbohydrate and Protein Blotting:

The potential effects of thioredoxin treatments on mucin fine structure is assessed by performing protein blotting analysis on intact HBE mucus. 50-200 µL aliquots of samples are loaded onto nitrocellulose membranes and a vacuum applied for five min to pull the entire loaded sample into the membrane. Samples are washed 2× in distilled water. For periodic acid Schiff's (PAS) assays of carbohydrate content, loaded and washed samples are incubated for 30 minutes in 0.25% periodic acid+3% acetic acid in water. Following two distilled water washes, samples are incubated in NaMBS solution (0.1% sodium metabisultate, 1% HCl) twice for five minutes. Next, samples are incubated with Schiff's reagent for 5-15 min and washed twice in NaMBS, once in distilled water, and quickly vacuum dried. Protein-specific antibody blots are blocked with 1% milk in TBST buffer (1.21% Tris HCl, 8.76% NaCl, and 0.5% Tween, pH 8) following loading and the first distilled water washes. After two five-min TBST washes, samples are incubated in primary antibody (MAN-5ACI for MUC5AC, MUC5BIII and K5B for MUC5B) for 30 min. Following two additional five-min washes in TBST, samples are incubated in secondary antibody for two hours. Membrane blots are developed using a Li-Cor Odyssey infrared detector. Additionally, anti-thioredoxin antibodies may be used to detect monocysteinic vs. native thioredoxin bound to mucins. Compared to standard Western immunoblotting following separation on PAGE gels this direct blotting approach allows for more rapid and precise determination of mucin content and to visualize and quantify covalent interaction between monocysteinic active site thioredoxin (r(Cys)hTrx) and mucin disulfide bonds.

Example 8

This example demonstrates the ability of monocysteinic active site Trx (r(Cys)hTrx) to attenuate the propensity of native rhTrx to induce proinflammatory and pathophysiological effects in the lung following intratracheal delivery to rats and mice.

Evaluation of Pro-Inflammatory Cytokine Release and Cell Migration in Normal Rats Dosed Intratracheally with r(Cys)hTrx and Native rhTrx.

To determine r(Cys)hTrx's ability to induce pro-inflammatory signaling as compared to native rhTrx, a comparative in vivo study in rats utilizing intratracheal (IT) delivery of increasing concentrations of thioredoxin protein compared to vehicle control is performed. The two study components are 1) an initial study designed to replicate previous findings (Rancourt, R. et al., *Free Radic Biol Med,* 42(9):1441-1453, 2007) obtained with purified native rhTrx, and 2) a Main Study to compare the pro-inflammatory effects of r(Cys)hTrx to native rhTrx. All studies utilize purified, endotoxin-free protein that has been treated with DTT or other suitable reductant to reduce (activate) the Trx active site Cys residues. Following reduction, DTT or reductant is removed via size-exclusion chromatography. Full reduction of Trx Cys residues is verified by in vitro assay (DTNB reduction) and catalytic disulfide-bond reduction activity of r(Cys)hTrx is assayed using an insulin-reduction or HPLC target-binding assay.

Initial Study: Twenty-four rats are randomized into four experimental groups with six animals per group dosed as follows: Group 1 vehicle control; Group 2 oxidized (inactive) rhTrx; Group 3 reduced (active) rhTrx; Group 4 Human Serum Albumin (HSA; negative control). All test articles are delivered once by the IT route. The end points of this study include 1) cytokine analysis of TNF, cytokine induced neutrophil chemo-attractant-2 (CINC2) and macrophage inflammatory protein-3 (MIP3) by enzyme-linked immunosorbent assays (ELISA); and 2) cell counts from bronchoalveolar lavage (BAL) with Wright's staining to elucidate the percentage of inflammatory cells (neutrophil vs macrophage). Group 2 (treated with oxidized rhTrx) has a similar level of cytokine activities and cell counts in BAL compared to Group 1, the vehicle control and Group 4, HSA. Group 3, treated with a reduced rhTrx has an increased level of cytokine activities and cell counts compared to Group 1 and Group 2.

Main Study: Comparison of cytokine release in rats when administered native thioredoxin rhTRX vs. r(Cys)hTRX. In this comparative study, the relative degree of in vivo cytokine release and cell migration following IT administration for rhTrx vs. r(Cys)hTrx is determined. Three dose levels of reduced rhTrx and reduced r(Cys)hTrx are tested (50 µM, 200 µM and 1000 µM). End points are the same as for the Pilot study with the addition of immunohistochemistry (IHC) analysis of lung tissues. In r(Cys)hTrx mutation of the C-terminal active site cysteine motif (change CXXC to CXXX) has been shown to eliminate the second thiol-disulfide exchange capability of thioredoxin and results in covalent linkage to disulfide-bond targets. The most prominent extracellular disulfide-bond targets in the lung, which IT-delivered TRX encounters first, are located in the mucus layer and on epithelial cell-surface proteins. Consequently, as compared to native rhTrx, an increased binding of r(Cys)hTrx to lung epithelial cells and associated mucus occurs and this binding may be detected by IHC using an anti-human thioredoxin antibody. Lung tissues are collected from two animals from each group for IHC analysis without BAL and compared to two post-BAL animals from each of the same groups. Hence, for each group eight animals are lavaged, and two animals are treated but not subject to BAL prior to lung collection and IHC. r(Cys)hTrx exhibits an attenuated dose-dependent ability to increase cytokine activities and cell counts compared to the same dose level of rhTrx.

Evaluation of Toxicity and Lung Pathology in Normal Rats Dosed Intratracheally with r(Cys)hTrx.

To assess pulmonary effects of r(Cys)hTrx under exaggerated dosing conditions a range of single doses of r(Cys)hTrx from 0.5 to 20 mg/kg is administered by the IT route, and evaluation of whether pathological changes have occurred at 2 and 14 days post-dosing is performed. Male and female Sprague-Dawley rats are randomized into three experimental groups with 20 animals per group (10/sex). All animals are given a pre-study physical examination. Vehicle (saline formulation) is used as a negative control. The end points of this study include 1) clinical and histopathological examination to look for gross adverse changes; and 2) characterization of serum to detect the presence of test article and antibodies to the test article. Monocysteinic r(Cys)hTrx results in less severe effects at comparable dosages vs. native rhTrx.

Evaluation of Pro-Inflammatory Cytokine Release and Cell Migration in Normal and bENaC Mice Dosed Intratracheally with r(Cys)hTrx and Native rhTrx.

Mice are briefly anesthetized with isoflurane and placed on a tilting rodent workstation. Using a rodent laryngoscope fitted with a magnifying loupe, the larynx is directly visualized and a microsprayer (PennCentury) is passed into the distal trachea. A fixed volume (25-50 µL) of test article solution is administered in the airway and the mice allowed to recover. Weight at time of airway instillation and euthanasia is recorded. Following Institutional Animal Care and Use Committee (IACUC) approved protocols, five mice per condition are euthanized at six hours and another five mice at 24 hours after IT instillation. The airways are lavaged with a total of 1.5 mL of cold, sterile saline with protease inhibitor (Pierce). Whole lungs are collected and all specimens are stored on ice until processed further. Bronchoalveolar lavage fluid (BALF) is centrifuged to pellet leukocytes and other cell debris. Cell-free BALF is frozen at −80C until ELISA testing is performed. The BAL cell pellet is resuspended in 1 mL of sterile saline and total leukocyte counts with differentials are performed using a Coulter counter and manual counts of 300 cells from stained cytospin preparations. When all samples have been collected, BAL fluid is thawed on ice and ELISAs are performed for KC (analog of IL-8), TNF alpha, IL-6, and IL-1beta (ElisaTech, Denver, Colo.). BALF cellularity is characterized by both % and total leukocytes (neutrophils, macrophages, lymphocytes).

Both wild-type and mutant TRX are tested at two concentrations and two time points, along with control animals, to determine the acute airway inflammatory response to both mutant and wildtype TRX, relative to diluent control (Table 2). The response is characterized by: change in body weight, total leukocyte count in BALF, relative and total neutrophil, macrophage, and lymphocyte counts, and the inflammatory cytokines listed above. r(Cys)hTrx exhibits an attenuated dose-dependent ability to increase cytokine activities and cell counts, as well as adverse effects, compared to the same dose level of rhTrx.

TABLE 2

| | Diluent Control | rhTrx (500 µM) | r(Cys)hTrx (10 µM) | r(Cys)hTrx (250 µM) | r(Cys)hTrx (1000 µM) |
|---|---|---|---|---|---|
| 6 hr | 5 | 5 | 5 | 5 | 5 |
| 24 hr | 5 | 5 | 5 | 5 | 5 |

Evaluation of Pathophysiological and Inflammatory Effects in Normal and βENaC Mice Dosed Intratracheally with r(Cys)hTrx and Native rhTrx.

Previous studies by Rancourt and colleagues (Rancourt, R. et al., *Free Radic Biol Med*, 42(9):1441-1453, 2007) demonstrated that the presence of additional (exogenous) mucus on the airways could significantly reduce the stimulation of cytokine release by native Trx. While this might suggest that CF patients with a higher mucus burden might exhibit a reduced inflammatory response due to extracellular reduction of the Trx, there is currently no information regarding the effect of thioredoxin in an airway model with 1) increased endogenous mucus production and 2) a preexisting inflammatory response (as in CF). The goal of these studies is to use a mouse model of chronic mucus obstruction/inflammation to investigate the effect of native Trx and r(Cys)hTrx. For these studies, the βENaC mouse model which overexpresses the Beta subunit of the ENaC channel and exhibits water hyperasborption in the lungs is used (Mall, M., et al., *Nat Med.* 10(5):487-493, 2004). The βENaC mice produce excess mucus and develop a CF/COPD-like lung phenotype with mucus airway plugging and inflammation. These mice have previously been used as a model of CF lung disease in a number of preclinical studies (e.g., Graeber, S. Y., et al., *Am J Respir Cell Mol Biol* 49(3):410-417, 2013). In the present study 1) the effect of native Trx vs r(Cys)hTrx on airway/lung histopathology and inflammation status; and 2) the effect of these agents on mucus burden in βENaC mice (see below) is determined to investigate the relative effect of native and monocysteinic Trx (r(Cys)hTrx) over a range of delivery doses and understand how chronic mucus overproduction and pre-existing inflammation modulates the potential pulmonary toxicities of these compounds.

The effects of three concentrations (100 μM, 500 μM and 1000 μM) of native thioredoxin in vivo using WT and βENaC mice and comparison of toxicity and drug efficacy with the r(Cys)hTrx compound at the same concentrations is determined. A minimum of seven mice per condition are tested. All compounds are administered via intratracheal instillation (10-25 μl) at a given concentration. A single dose treatment is used and toxicity and drug efficacy is monitored at four time points (4 h, 24 h, 72 h and 7 days post-dosing). Early time points (4 h-24 h) are carefully monitored. Later time points (72 h-Day 7) are monitored if drug toxicity is maintained at 24 h. The effects of the lower concentrations (100 μM, 500 μM) are expected to not be sustained past 24 h or Day 3, respectively. The protocol used allows instillation of volumes as small as 10 μl reliably into mouse lungs. Briefly, the animals are anesthetized with isoflurane, placed onto a mouse intubation platform wherein the retropharynx is visualized using a small laryngoscope. Drugs are instilled either directly into the trachea (intratracheal instillation, IT) or, for a more homogenous and deeper deposition, 25 μl are delivered by microspray using the Penn Century device. After treatment, animals are euthanized at the appropriate time point. Intact lungs are collected for histology and bronchoalveolar lavage fluids for various measurements, i.e., cell count, mucin content and reduction status and cytokines. In more details, the left lung is tied up via a ligature around the mainstem bronchus and surgically isolated for histology. A bronchoalveolar lavage of the opposite lung (or right lobes) is performed via a tracheotomy and cannula using 500 μl of sterile PBS. After fixation of the whole lung, longitudinal sections are analyzed by H&E and AB-PAS staining to assess inflammation and retained mucus. BALs are analyzed for cell counts/differentials, mucin content and reduction status (agarose gel separation method and Western blotting), and cytokines.

Sample size and statistical analysis: Each of the compounds are evaluated at various concentrations (100 μmol, 500 μmol, 1000 μmol) for a total of 7 mice per condition. Two groups are tested, wildtype (WT) and βENaC mice (Table 3). As indicated by "X's" in the following table a total of 36 conditions×7 mice (252 mice total) are treated and analyzed to provide a sufficient understanding of the inter- and intra-sample variation of each condition. For data analysis, comparison between individual samples/groups is made using two-tailed Student's t-test. For multiple group comparisons, a one-way analysis of variance (ANOVA) is used. Significance for all analyses will be set at $p<0.05$. Monocysteinic r(Cys)hTrx results in less severe effects at comparable dosages vs. native rhTrx, and this effect is further attenuated by the presence of endogenous mucus in the βENaC mice.

TABLE 3

| Model | Compound | Concn (μmol) | 4 h | 24 h | 72 h | Day 7 |
|---|---|---|---|---|---|---|
| WT | Thioredoxin | 100 | X | X | | |
| | | 500 | X | X | X | |
| | | 1000 | X | X | X | X |
| | r(Cys)hTrx | 100 | X | X | | |
| | | 500 | X | X | X | |
| | | 1000 | X | X | X | X |
| βENaC | Thioredoxin | 100 | X | X | | |
| | | 500 | X | X | X | |
| | | 1000 | X | X | X | X |
| | r(Cys)hTrx | 100 | X | X | | |
| | | 500 | X | X | X | |
| | | 1000 | X | X | X | X |

"X" represents times x concentrations tested

Example 9

This example demonstrates that r(Cys)hTrx improves mucus-normalizing activity versus wildtype rhTrx. The effect of wildtype rhTrx, r(Cys)hTrx and various controls including dithiothreitol (DTT) at two concentrations, N-acetyl cysteine (NAC) and recombinant human DNase (rhDNase) at equimolar concentrations on normalization of patient sputum samples (n=6 per treatment) in a sputum-compaction assay was determined. Sputum studies were conducted using four to six spontaneously-expectorated (non-induced) samples each from up to three individual CF patients for each experiment. The "favorable" part of the sputum (i.e. the mucus) was collected and combined from each sample and the total sample is gently homogenized by stifling or mild vortexing before separating into tubes and exposing to either: diluent (i.e. Tris buffer), DTT in diluent (at 0.58 mM and 1.5 mM), NAC in diluent (0.58 mM), rhDNase in diluent (0.58 mM), rhTrx in diluent (0.58 mM) or r(Cys)hTrx (referred to as ORP-100) in diluent (0.58 mM). DTT was made fresh for each experiment as a positive control. FIG. 2 shows that r(Cys)hTrx was able to increase markedly the liquefaction of patient sputum as compared to wildtype thioredoxin (referred to as "rhTrx" in FIG. 2), thus showing an improved mucus-normalizing activity versus both native Trx and the standard of care recombinant human DNase, Pulmozyme™ ("rhDNase"). Both thioredoxin and DNase were in turn more potent than equimolar amounts of NAC, commonly used as a mucolytic outside of the US. These results using human CF patient sputum demonstrate that monocysteinic r(Cys)hTrx remains fully competent for CF sputum viscoelasticity normalization (and is even more potent than unmodified native rhTrx), despite the expected covalent binding to mucin Cys. However, the potential for the small 12 kD r(Cys)hTrx to cross the lung epithelium should be greatly minimized by binding to mucin. The ability of active r(Cys)hTrx to then subsequently enter the cell nucleus and interact with redox regulatory target proteins such as NFkB is even further attenuated, as is any signaling due to interaction with extracellular transmembrane domains on immune cells as has been theorized for Trx-mediated activation of the CD30 TNF receptor (Schwertassek, U., et al., *EMBO J* 26(13):3086-3097, 2007). The increased potency observed for r(Cys)hTrx (FIGS. 1a, 1b and 2) is consistent with mucin Cys covalent binding by the molecule, as bound Cys would be blocked from re-forming disulfide bonds unlike treatment with native rhTrx (or indeed, any small-molecule thiol agent).

Each of the publications and other references discussed or cited herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to decrease viscoelasticity of mucus or sputum in a patient that has excessively viscous or cohesive mucus or sputum, comprising contacting the mucus or sputum of the patient with a composition comprising a protein or peptide containing a thioredoxin monocysteinic active site in a reduced state effective to decrease the viscoelasticity of the mucus or sputum as compared to prior to the step of contacting, wherein the thioredoxin monocysteinic active site comprises an amino acid sequence selected from the group consisting of C-X-X-S (SEQ ID NO:24), C-X-X-X (SEQ ID NO: 17), X-C-X-X-X-X (SEQ ID NO: 19), X-C-G-P-X-X (SEQ ID NO: 21), W-C-G-P-X-K (SEQ ID NO: 23), X-C-X-X-S-X (SEQ ID NO: 25), X-C-G-P-S-X (SEQ ID NO: 26), and W-C-G-P-S-K (SEQ ID NO: 27), wherein the C residue is in a reduced state, and wherein the X residues are any amino acid residue other than cysteine.

2. The method of claim 1, wherein the patient has a lung disease in which abnormal or excessive viscosity or cohesiveness of mucus or sputum is a symptom or cause of the disease.

3. The method of claim 1, wherein the patient has a lung disease in which abnormal or excessive viscosity or cohesiveness of mucus or sputum is associated with a deficiency of biological reductant activity.

4. The method of claim 1, wherein the patient has a disease selected from the group consisting of cystic fibrosis, chronic obstructive pulmonary disease, bronchiectasis, asthma and a digestive tract disease.

5. The method of claim 1, wherein the patient has cystic fibrosis.

6. The method of claim 1, wherein the step of contacting the mucus or sputum of the patient with the composition is performed by introducing the composition to the patient by a route selected from the group consisting of nasal, intratracheal, bronchial, direct installation into the lung, and inhaled.

7. The method of claim 1, wherein the mucus or sputum to be contacted is located in the respiratory tract of the patient.

8. The method of claim 1, wherein the composition is administered to the patient in a pharmaceutically acceptable carrier.

9. The method of claim 1, wherein the step of contacting the mucus or sputum of the patient with the composition increases the percentage of free thiols in a sample of mucus or sputum from the patient as compared to prior to contact with the composition.

10. The method of claim 1, wherein after the step of contacting the mucus or sputum of the patient with the composition the patient has at least about a 2.5% increase in forced expiratory volume (FEV) as compared to prior to the step of contacting.

11. The method of claim 1, wherein the thioredoxin monocystic active site comprises an amino acid sequence consisting of C-X-X-X (SEQ ID NO: 17, wherein the C residue is in a reduced state, and wherein the X residues are any amino acid residue other than cysteine.

12. The method of claim 1, wherein the thioredoxin monocysteinic active site comprises the amino acid sequence C-X-X-S (SEQ ID NO: 24), wherein the C residue is in a reduced state, and wherein the X residues are any amino acid residue other than cysteine.

13. The method of claim 1, wherein the protein or peptide containing a thioredoxin monocysteinic active site covalently binds to a cysteine residue in a mucus protein.

14. The method of claim 13, wherein the mucus protein is a mucin.

15. The method of claim 13, wherein the mucus protein is a respiratory mucus protein.

16. The method of claim 1, wherein the protein comprises human thioredoxin.

17. The method of claim 1, wherein the patient is a human.

* * * * *